(12) United States Patent
Zhang et al.

(10) Patent No.: US 7,531,802 B2
(45) Date of Patent: May 12, 2009

(54) METHOD OF ANALYZING A REMOTELY-LOCATED OBJECT UTILIZING AN OPTICAL TECHNIQUE TO DETECT TERAHERTZ RADIATION

(75) Inventors: Xi-Cheng Zhang, Melrose, NY (US); Jianming Dai, Troy, NY (US); Xu Xie, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 336 days.

(21) Appl. No.: 11/610,824

(22) Filed: Dec. 14, 2006

(65) Prior Publication Data

US 2007/0145276 A1  Jun. 28, 2007

Related U.S. Application Data

(60) Provisional application No. 60/754,096, filed on Dec. 27, 2005.

(51) Int. Cl.
  *G01N 21/35* (2006.01)
(52) U.S. Cl. .................................. 250/341.1
(58) Field of Classification Search .............. 250/341.1
  See application file for complete search history.

(56) References Cited

U.S. PATENT DOCUMENTS 5,939,721 A * 8/1999 Jacobsen et al. ............ 250/330
6,111,416 A    8/2000 Zhang et al.
6,977,379 B2   12/2005 Zhang et al. ............ 250/341.1
2005/0242287 A1 * 11/2005 Hakimi .................. 250/363.09

FOREIGN PATENT DOCUMENTS

| GB | 2396695 | 6/2004 |
| GB | 2399626 | 9/2004 |
| WO | 0075641 | 12/2000 |

OTHER PUBLICATIONS

G. Méchain, A. Mysyrowicz, M. Depiesse, M. Pellet, "A virtual antenna produced in air by intense femtosecond laser pulses," (Nov. 3, 2005) Proc. SPIE, Vo. 5989, 59890S (2005) DOI:10.1117/12.631202 (6 pages).*

(Continued)

*Primary Examiner*—Constantine Hannaher
(74) *Attorney, Agent, or Firm*—Heslin Rothenberg Farley & Mesiti P.C.

(57) ABSTRACT

A method of analyzing a remotely-located object includes the steps of inducing a volume of an ionized ambient gas to emit pulsed terahertz radiation directed toward a targeted object by focusing an optical pump beam in the volume and ionizing another volume of the ambient gas to produce a sensor plasma by focusing an optical probe beam in the other volume of ambient gas. The interaction, in the sensor plasma, of the focused optical probe beam and an incident terahertz wave, which is produced by the targeted object reflecting, scattering, or transmitting the pulsed terahertz radiation, produces a resultant radiation. Detecting an optical component of the resultant radiation emitted by the sensor plasma facilitates detection of a signature of the targeted object imposed onto the incident terahertz radiation.

41 Claims, 18 Drawing Sheets

OTHER PUBLICATIONS

Zandonella, Catherine, "T-Ray Specs," Nature, vol. 424, pp. 721-722, Aug. 14, 2003.
Bartel et al., "Generation of Single-Cycle THZ Transients with High Electric-Field Amplitudes," Optics Letters, vol. 30, No. 20, 3-pages, Oct. 15, 2005.
Cook et al., "Intense Terahertz Pulses by Four-Wave Rectification in Air," Optics Letters, vol. 25, No. 16, pp. 1210-1212, Aug. 15, 2000.
Dai et al., "Detection of Broadband Terahertz Waves with a Laser-Induced Plasma in Gases," Physical Review Letters, 4-pages, Sep. 8, 2006.
Ferguson et al., "Materials for Terahertz Science and Technology," Nature Materials, vol. 1, pp. 26-33, Sep. 2002.
Hamster et al., "Short-Pulse Terahertz Radiation from high-Intensity-Laser-Produced Plasmas," Physical Review, vol. 49, No. 1, pp. 671-677, Jan. 1994.
Janke et al., "Inversionless Amplification of Coherent Terahertz Radiation," Physical Review Letters, vol. 67, pp. 155206-1 to 155206-4, 2003.
Kress et al., "Determination of the Carrier-Envelope Phase of Few-Cycle Laser Pulses with Terahertz-Emission Spectroscopy," Nature Physics, vol. 2, pp. 327-331, May 2006.
Kress et al., "Terahertz-Pulse Generation by Photoionization of Air with Laser Pulses Composed of Both Fundamental and Second-Harmonic Waves," Optics Letters, vol. 29, No. 10, pp. 1120-1122, May 15, 2004.
Löffler et al., "Efficient Terahertz Pulse Generation in Laser-Induced Gas Plasmas," Acta Physica Polonica A, vol. 107, No. 1, pp. 99-108, 2005.
Martini et al., "Inversionless Amplification of Coherent THz Radiation," IEEE, pp. 242-245, 1998. THz 98, IEEE 6th Intl Conf on THz Electronics, Sep. 3-4, 1998.
Meyer et al., "Phase-Matched High-Order Difference-Frequency Mixing in Plasmas," Physical Review Letters, vol. 26, No. 18, pp. 3336-3339, Apr. 29, 1996.
Théberge et al., "Tunable Ultrashort Laser Pulses Generated Through Filamentation in Gases," Physical Review Letters, Vol. 97, pp. 023904-1 to 023904-5, Jul. 14, 2006.
Tzortzakis et al., "Coherent Subterahertz Radiation from Femtosecond Infrared Filaments in Air," Optics Letters, vol. 27, No. 21, pp. 1944-1946, Nov. 1, 2002.
Van Exter et al., "High-Brightness Terahertz Beams Characterized with an Ultrafast Detector," Applied Physics Letters, vol. 55, No. 4, pp. 337-339, Jul. 24, 1989.
Wu et al., "Broadband Detection Capability of ZnTe Electro-Optic Field Detectors," Applied Physics Letters, vol. 68, No. 21, pp. 2924-2926, May 20, 1996.
Xie et al, "Coherent Control of THz Wave Generation in Ambient Air," Physical Review Letters, vol. 96, pp. 075005-1 to 075005-4, Feb. 24, 2006.
Xie et al., "Enhancement of Terahertz Wave Generation from Laser Induced Plasma," Applied Physics Letters, vol. 90, 2007, 141104, 3-pages, Apr. 4, 2007.
Zhang et al., pending U.S. Appl. No. 11/756,230, filed May 31, 2007, entitled "Methods and Systems for the Enhancement of Terahertz Wave Generation for Analyzing a Remotely-Located Object".
Zhang et al., pending U.S. Appl. No. 11/756,243, filed May 31, 2007, entitled "Methods and Systems for Generating Amplified Terahertz Radiation for Analyzing Remotely-Located Objects".
Zhu et al., "Long Lifetime Plasma Channel in Air Generated by Multiple Femtosecond Laser Pulses and an External Electrical Field," Optics Express, vol. 14, No. 11, pp. 4915-4922, May 29, 2006.
Agrawal, Govind P., "Nonlinear Fiber Optics," Third Edition, Academic Press, San Diego, 1-page, 2001, cover only.
Reimann, et al., "Direct Field-Resolved Detection of Terahertz Transients with Amplitudes of Megavolts per Centimeter," Optics Letters, vol. 28, No. 6, pp. 471-473, Mar. 15, 2003.
Carr et al., "High-Power Terahertz Radiation From Relativistic Electrons," Nature, vol. 420, pp. 153-156, Nov. 2002.
Chin et al., "The Propagation of Powerful Femtosecond Laser Pulses in Optical Media: Physics, Application, and New Challenges [1,2]," Canadian Journal of Physics, vol. 83, No. 9, pp. 863-905, Sep. 2005.
Cole et al., "Coherent Manipulation of Semiconductor Quantum Bits with Terahertz Radiation," Nature, vol. 410, pp. 60-63, Mar. 2001.
Cook et al., "Terahertz-Field-Induced Second-Harmonic Generation Measurements of Liquid Dynamics," Chemical Physics Letters, vol. 309, pp. 221-228, Aug. 13, 1999.
Grischkowsky et al., Far-infrared Time-Domain Spectroscopy with Terahertz Beams of Dielectrics and Semiconductors, J. Optical Society America B, vol. 7, No. 10, pp. 2006-2015, Oct. 1990.
Huber et al., "How Many-Particle Interactions Develop After Ultra Fast Excitation of an Electron-Hole Plasma," Nature, Vol. 414, pp. 286-289, Nov. 2001.
Kaindl et al., "Ultrafast terahertz Probes of Transient Conducting and Insulation Phases in an Electron-Hole Gas," Nature, vol. 423, pp. 734-738, Jun. 12, 2003.
Köhler et al., "Terahertz Semiconductor-Heterostructure Laser," Nature, vol. 417, pp. 156-159, May 9, 2002.
Nahata et al., "Detection of Freely Propagating Terahertz Radiation by Use of Optical Second-Harmonic Generation," Optics Letters, vol. 23, No. 1, pp. 67-69, Jan. 1, 1998.
Wang et al., "Metal Wires for Terahertz Wave Guiding," Nature, vol. 432, pp. 376-379, Nov. 18, 2004.
Wu et al., "Free-Space Electro-Optic Sampling of Terahertz Beams," American Physics Letters, vol. 67, No. 24, pp. 32523-3525, Dec. 11, 1995.
Zhong et al., "Terahertz Emission Profile From Laser-Induced Air Plasma," Applied Physics Letters, vol. 88, pp. 261103-1-261103-3, 2006.
Hamster et al., "Subpicosecond, Electromagnetic Pulses from Intense Laser-Plasma Interaction," Physical Review Letters, vol. 71, No. 17, pp. 2725-2728, Oct. 25, 1993
Walsh et al., "The Tunnel Ionization of Atoms, Diatomic and Triatomic Molecules Using Intense 10.6 ∥m Radiation," Phys. B: At. Mol. Opt. Phys. Vol. 27, pp. 3767-3779, 1994.
International Search Report based on PCT/US2006/062091, not a plublication.
Federicii, John F. et al., "THz Standoff Detection and Imaging of Explosives and Weapons," Optics and Photonics in Global Homeland Security, vol. 5781 pp. 75-84, Proc. SPIE vol. 5781 (2005).

* cited by examiner

METHOD OF ANALYZING A REMOTELY-LOCATED OBJECT UTILIZING AN OPTICAL TECHNIQUE TO DETECT TERAHERTZ RADIATION

CROSS-REFERENCE TO RELATED APPLICATIONS

This application claims priority under 35 U.S.C. §119 to U.S. Provisional Application No. 60/754,096, filed Dec. 27, 2005, which is herein incorporated by reference in its entirety.

GOVERNMENT RIGHTS STATEMENT

This invention was made with U.S. Government support under Grant No. ECS-0621522 from the National Science Foundation and Grant No. DAAD 19-02-1-0255 from the Army Research Office. The U.S. Government has certain rights in the invention.

BACKGROUND OF THE INVENTION

1. Technical Field

The present invention generally relates to generating and detecting terahertz radiation. More particularly, the present invention relates to utilizing optical-wavelength radiation to facilitate remote analysis of an object with terahertz radiation.

2. Background Information

Improvised explosive devices (IEDs) are extremely dangerous partially because they are difficult to identify. A device capable of remote and in situ monitoring to detect concealed explosives would be very beneficial for a number of defense and homeland security uses.

Since terahertz wave spectroscopy has been utilized to detect a number of chemical and explosive materials and related compounds by providing their spectral signatures in the terahertz frequency range, it may have use in defense and security applications. For example, there is interest in terahertz wave spectroscopy as a technique to sense improvised explosive devices (IEDs). However, due to the severe water vapor attenuation of terahertz waves in the atmosphere, the reliable sensing range of terahertz wave spectroscopy has been limited to relatively short distances. For example, even though propagation of a pulsed terahertz wave for more than 145 meters has been achieved, spectroscopic measurement with an acceptable signal-to-noise ratio and false alarm rate is limited to about 30 meters. For defense and security applications, it is desirable to increase the reliable sensing range of terahertz wave spectroscopy. Thus, there is a need for a technique to increase the range at which terahertz waves may be reliably sensed under a range of atmospheric conditions and to decrease the sensitivity to the humidity level.

SUMMARY OF THE INVENTION

Briefly, the present invention satisfies the need for a technique that increases the range at which terahertz waves may be reliably sensed under a range of atmospheric conditions.

The present invention provides, in one aspect, a method of and system for detecting terahertz radiation. The method includes the step of ionizing a volume of an ambient gas to produce a sensor plasma by focusing an optical probe beam in the volume and the step of detecting an optical component of resultant radiation produced from an interaction of the focused optical probe beam and an incident terahertz wave in the sensor plasma.

In another aspect, the present invention provides a method of and system for analyzing a remotely-located object. The method includes the steps of inducing an ionized volume of an ambient gas to emit pulsed terahertz radiation directed toward a targeted object by focusing an optical pump beam in the volume and ionizing another volume of the ambient gas to produce a sensor plasma by focusing an optical probe beam in the other volume of ambient gas. The method also includes detecting an optical component of resultant radiation produced from an interaction in the sensor plasma of the focused optical probe beam and an incident terahertz wave, which wave is produced by an interaction of the pulsed terahertz radiation with the targeted object. For example, the targeted object may reflect, scatter, or transmit the pulsed terahertz radiation to produce the incident wave to the sensor plasma.

In a third aspect, the present invention provides a method of analyzing a remotely-located object that includes inducing a volume of an ionized ambient gas to emit pulsed terahertz radiation directed toward a targeted object by focusing an optical pump beam in the volume; focusing an optical probe beam in the same volume of the ionized ambient gas produced by the optical pump beam; and detecting an optical component of resultant radiation produced from an interaction of the focused optical probe beam and an incident terahertz wave in the volume of the ionized ambient gas, wherein the incident terahertz wave is produced by an interaction of the pulsed terahertz radiation with the targeted object.

These, and other objects, features and advantages of this invention will become apparent from the following detailed description of various aspects of the invention taken in conjunction with the accompanying drawings.

DETAILED DESCRIPTION

Figure 1A:
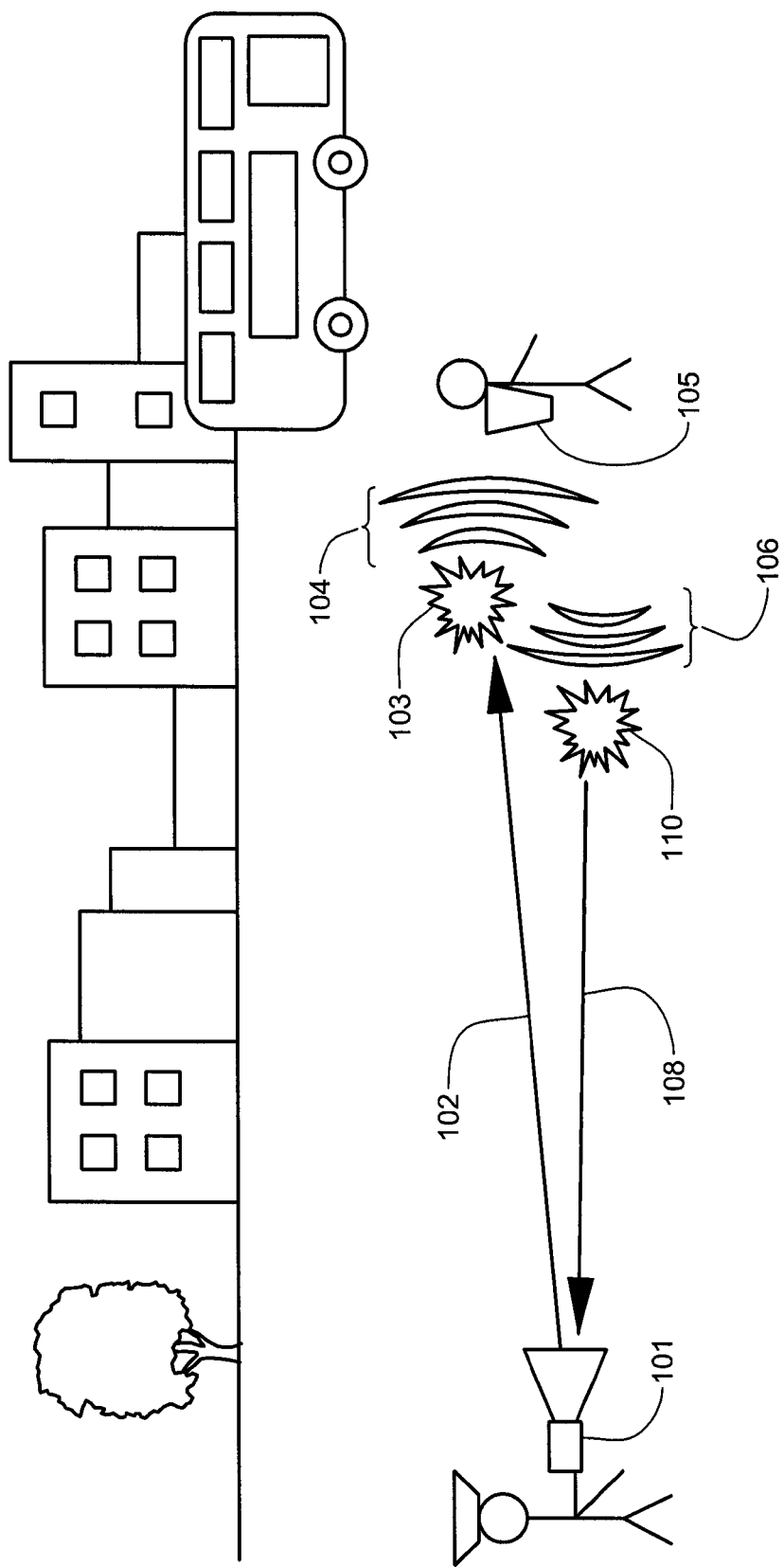
FIG. 1A illustrates one embodiment of a system for remotely analyzing an object in an exemplary environment in which the system may be used, wherein terahertz waves reflected by an object are detected.

Pulsed terahertz wave spectroscopy is capable of sensing at short ranges compounds from which improvised explosive devices (IEDs) may be made. For example, the compound RDX has been detected at distances up to 30 meters in good weather, but the detection range using terahertz radiation may decrease to less than 10 meters in humid conditions. The reason is that the propagation of a terahertz wave in air is largely limited by water vapor absorption. For example, the attenuation of terahertz waves through the atmosphere is greater than 100 dB/km, even when the humidity level is only 20% around room temperature. Measurements of the attenuation effect at humidity levels from 3% to 100% indicate that, in ambient air, it may not be practical to get useful terahertz spectroscopy information from a terahertz wave traveling more than 100 meters. On the other hand, optical pulses (i.e. pulses of visible light, for example) have a significantly lower attenuation (on the order of 0.01 dB/km) than terahertz waves in the air. Because optical pulses may be used to induce the generation of terahertz waves and to sense the incidence of terahertz waves, in accordance with the present invention, optical radiation may be used advantageously in terahertz spectroscopy for remote generation and detection of terahertz waves to solve the problem of high attenuation of terahertz radiation in the atmosphere and thereby increase the effective range at which terahertz spectroscopy can detect explosive materials.

In one aspect, the present invention provides a technique to detect terahertz radiation by detecting optical radiation that results from an interaction of the terahertz radiation with an optical probe beam. In another aspect, the present invention provides a technique that utilizes a combination of terahertz radiation, which is generated in close proximity to a targeted object by focusing a pulsed laser beam to ionize a volume of ambient gas close to the targeted object, and optical radiation to detect explosives and explosive related compounds from a distance. In one embodiment, a pulsed laser provides optical beams for producing plasmas by ionizing ambient air about the focal points of the optical beams. One of the resulting plasmas of ionized ambient air is utilized as a terahertz wave emitter, and another of the resulting plasmas of ionized ambient air is utilized as terahertz wave sensor. By transmitting optical beams in close proximity to a target, terahertz waves can be generated and detected near the target, thereby reducing the water vapor attenuation. Coherent control of terahertz wave generation and terahertz wave coherent detection by using ionized air as a terahertz wave emitter and sensor, respectively, has been demonstrated in experiments by the inventors.

In one embodiment, femtosecond (fs) optical pulses from a laser source are utilized for producing emitter and sensor plasmas in an ambient gas such as air. The emitter plasma is induced to generate terahertz radiation near a targeted object that is directed at the targeted object, and the sensor plasma detects the terahertz wave that results from the terahertz radiation's interaction with the target. Interaction of the terahertz radiation with the target includes reflection, scattering, and transmission of the terahertz radiation by the target. An explosive or related compound is detected by identifying the specified spectral fingerprint of the material in the terahertz wave detected by the sensor plasma.

In accordance with an aspect of a technique to remotely detect explosive related compounds, an optical beam is transmitted through an ambient gas and focused in a volume of the ambient gas in close proximity to the target to generate terahertz radiation, rather than initially transmitting a terahertz wave in the air. Pulsed laser radiation may also be focused in another volume of the ambient gas near the target to provide a terahertz wave sensor, rather than initially detecting the terahertz radiation reflected, scattered, or transmitted by the target with a terahertz-radiation detector located near the laser source. This facilitates sensing or analyzing a target at a greater distance (for example, 100 meters and beyond), even where the atmospheric humidity is high. In one embodiment, a femtosecond-pulse laser is transmitted through the air and focused at a point near the target. The pulsed laser radiation ionizes a volume of the air near the target, and this ionized air (i.e. plasma) provides a terahertz wave emitter. Pulsed laser radiation may also be focused in another volume of the ambient gas to provide a terahertz wave sensor.

In one such embodiment, a pulsed laser beam from a laser source is split into two beams by an optical beam splitter to provide separate emitter and detector plasmas. One of the beams generates terahertz waves in the air near the target, and a second one detects terahertz waves at a desired position. The location of the focal point of an optical beam may be controlled by one or more optical focusing elements, and thus the location of the terahertz radiation source can be controlled. The focused optical beam produces air plasma (ionized gas molecules) from which a very intense, highly-directional, broadband terahertz wave is emitted. A sensor plasma produced by a focused optical beam that ionizes ambient gas in the vicinity of the target senses a terahertz wave that is incident to the sensor plasma. For example, the terahertz wave that is incident to the sensor plasma may be a result of the object reflecting, scattering, or transmitting a terahertz wave emitted by the emitter plasma. Also, the location of the sensor plasma can also be controlled by one or more optical focusing elements.

Figure 1B:
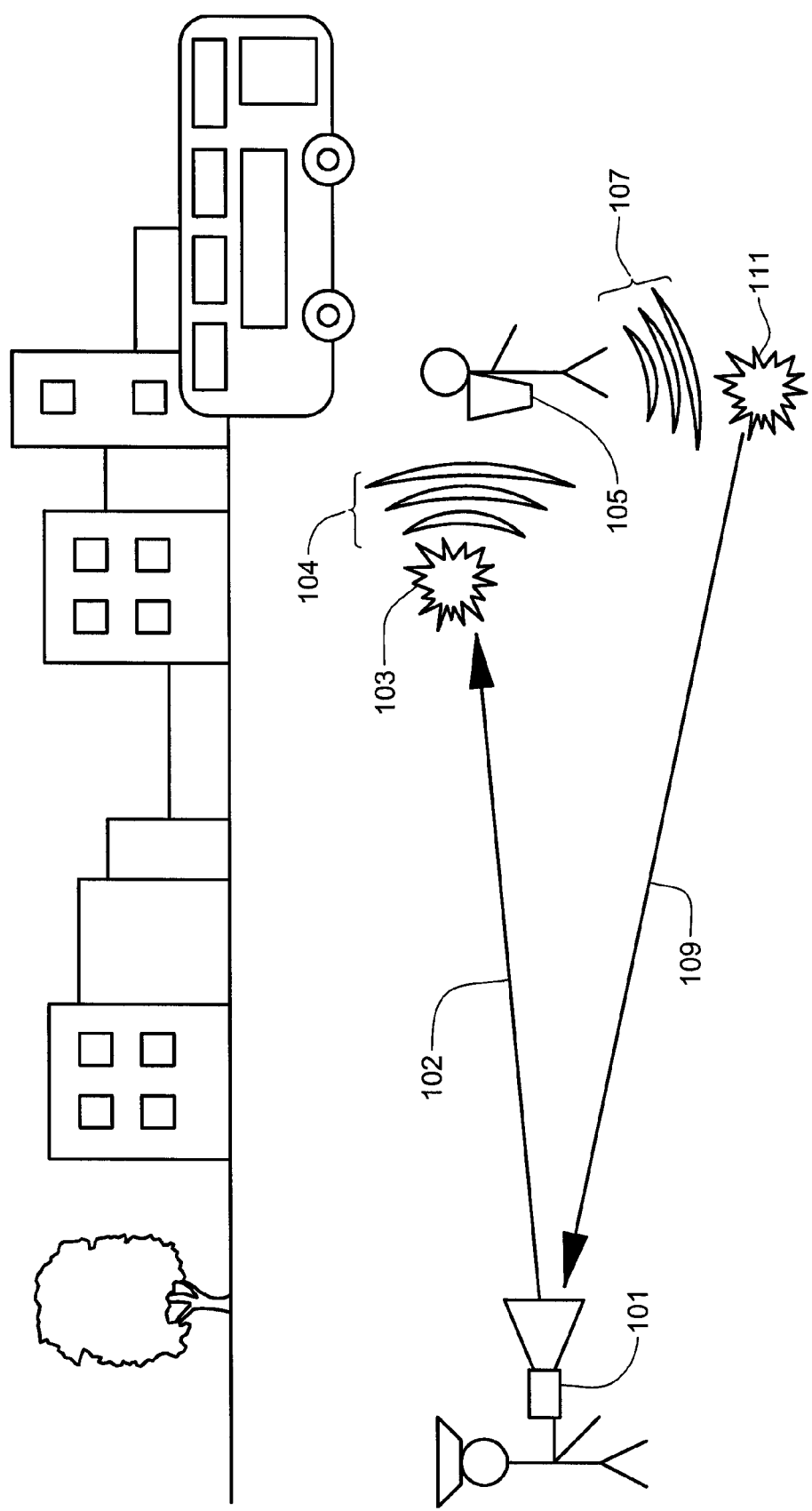
FIG. 1B illustrates one embodiment of a system for remotely analyzing an object in an exemplary environment in which the system may be used, wherein terahertz waves scattered by an object are detected.

FIGS. 1A and 1B illustrate one embodiment of a system 101 for remotely analyzing an object 105 in an exemplary environment in which the system may be used. In this embodiment, an operator directs an optical beam 102, rather than a terahertz beam, toward a target. The target reflects a portion of a terahertz wave 104 emitted by plasma 103 near the object. In FIG. 1A, a terahertz wave 106 reflected by the object is sensed by sensor plasma 110 near the object. The sensor plasma 110 emits an optical wave 108, which carries the spectral signature of the object that was imposed on the reflected terahertz wave. In FIG. 1B, a terahertz wave 107 scattered by the object is sensed by sensor plasma 111 near the object. The sensor plasma 111 emits an optical wave 109, which carries the spectral signature of the object that was imposed on the scattered terahertz wave. The optical radiation emitted by the sensor plasma is detected by the remote analysis system.

Figure 2:
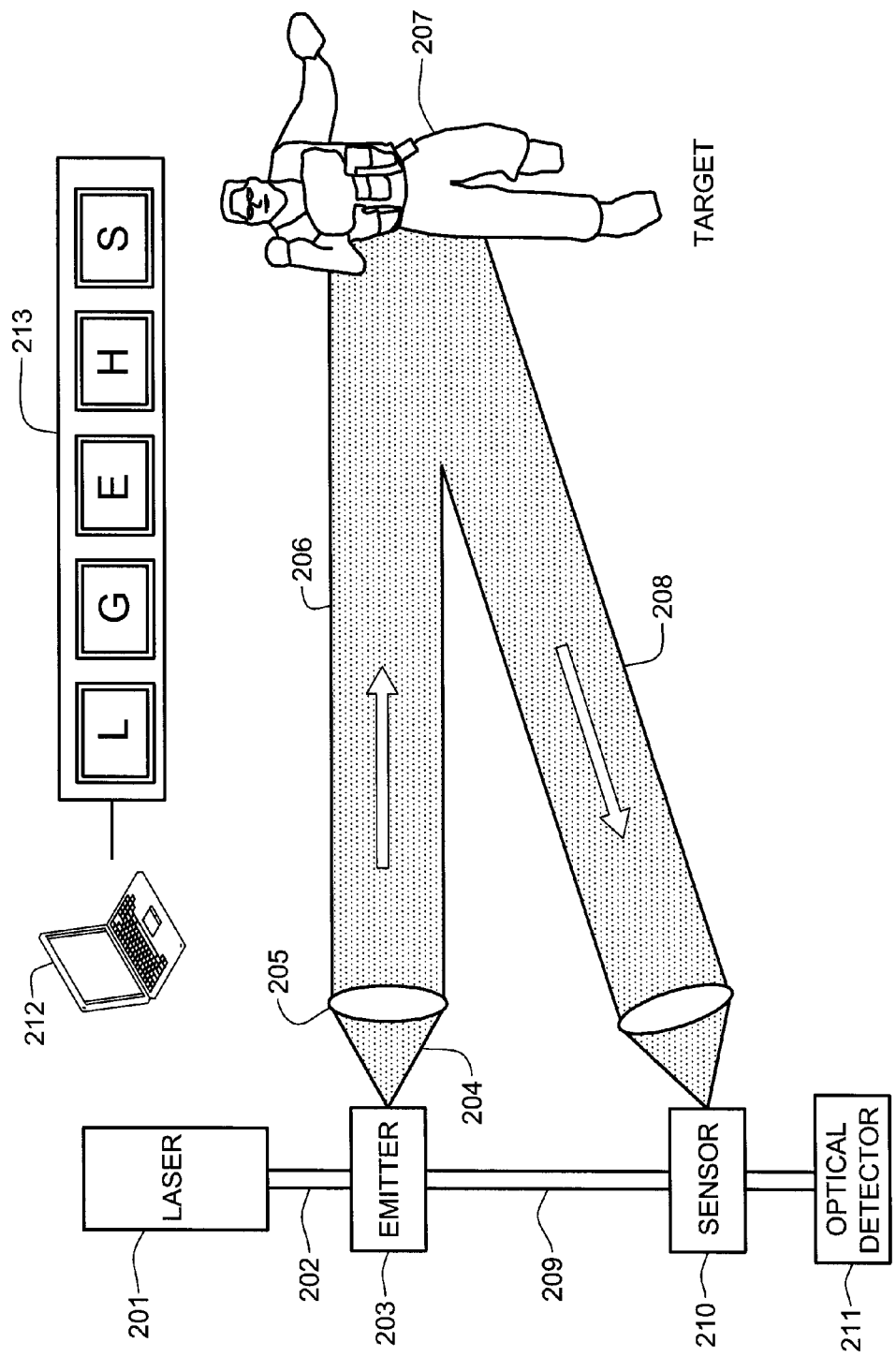
FIG. 2 illustrates another embodiment of a system for remotely analyzing an object in accordance with an aspect of the present invention.

FIG. 2 illustrates another embodiment of a system for remotely analyzing an object in accordance with an aspect of the present invention. In this embodiment, a laser source 201 provides an optical-wavelength pump beam 202 that is focused in a volume 203 of ambient gas. Excitation of the gas in volume 203 by optical pump beam 202 induces the excited gas to emit terahertz radiation. Emitted terahertz radiation 204 is directed to targeted object 207. Optionally, emitted terahertz radiation 204 may be concentrated by terahertz focusing device 205. Incident terahertz wave 206 interacts with targeted object 207, and targeted object 207 reflects a portion of incident terahertz wave 206 as reflected terahertz wave 208. In this embodiment, optical probe beam 209 is split from optical pump beam 202. Optical probe beam 209 is focused in another volume 210 of the ambient gas, wherein the gas is excited by optical probe beam 209 about its focal point. Reflected terahertz wave 208 is incident at volume 210, wherein the excited gas emits an optical signal comprising a second harmonic of the optical probe beam's frequency as a result of a nonlinear mixing of the optical probe beam and reflected terahertz wave. The optical signal emitted as a result of the nonlinear interaction of the optical probe beam and reflected terahertz wave may be detected with an optical detector 211, and computer 212 processes the detected optical signal to obtain the targeted object's signature. Computer 212 may provide display 213 with information pertaining to an analysis of the targeted object based on its detected signature. Optionally, reflected terahertz wave 208 may be focused in volume 210 by a terahertz focusing device.

Experimentation indicates that, after a threshold, the amplitude of the terahertz wave field emitted by plasma that is excited in accordance with an aspect of the present invention increases linearly with the power of the ionizing optical beam. In one embodiment, a signal-to-noise ratio of 100 to 1 was obtained using an amplified Ti:sapphire laser. In accordance with another aspect of the present invention, utilizing an optical beam comprising a fundamental frequency and its second harmonic to produce the plasma increases the strength of the resultant terahertz field. In one embodiment comprising a lens with a 200 mm focal length, the resultant terahertz field is highly directional with a diffraction angle of less than 6 degrees.

In accordance with an aspect of the present invention pertaining to analyzing a targeted object, an optically-induced terahertz wave illuminates at least a part of a target. As a result of the interaction of the optically-induced terahertz wave with the object, a spectral signature, such as a material's frequency absorption characteristic, is imposed on the spectrum of the terahertz wave reflected or scattered by the object. A second optical beam is focused at a location over 30 meters away from a laser source to sense the terahertz wave reflected or scattered by the object. Then, the optical radiation that is emitted by the sensor plasma in response to the incident reflected terahertz wave is detected, and the material's signature is identified in the detected optical radiation. Reliable, remote detection of a terahertz wave in air from a distance greater than 30 meters is facilitated by the imposition of the terahertz wave onto optical radiation as a modulation because the attenuation of optical radiation due to water vapor is much less than the attenuation of terahertz radiation.

In the sensor plasma about the focal spot of an optical probe beam, photons of the fundamental frequency (wavelength) radiation interact with terahertz wave photons to generate a second-harmonic optical wavelength photon through a third order optical nonlinear process. (Due to the isotropic property in the air, only the third order nonlinearity coefficient is non-zero). By measuring the time-resolved second harmonic optical intensity, the spectral signature information carried by the reflected terahertz wave may be decoded. Therefore, remote identification of objects such as an IED may be performed at a greater distance by transmitting an optical beam through the air to induce a local terahertz wave directed toward an object and receiving an optical beam to remotely detect a terahertz wave reflected or transmitted by the object. The measurements may comprise one more of the intensity, polarization, and phase of the second harmonic optical wave, for example.

Figure 3A:
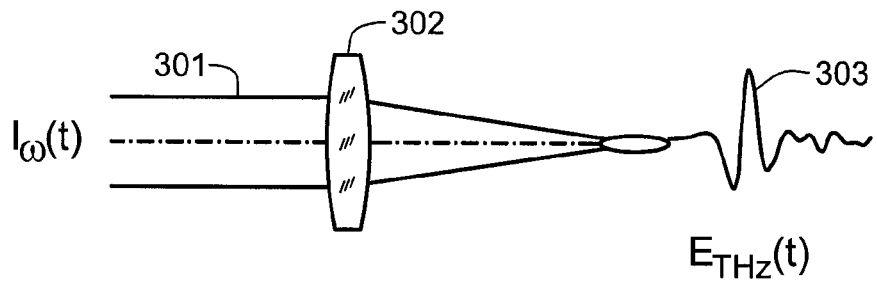
FIGS. 3A, 3B, and 3C illustrate techniques to generate terahertz radiation in an ambient gas by using optical beams, in accordance with an aspect of the present invention.
Figure 3B:
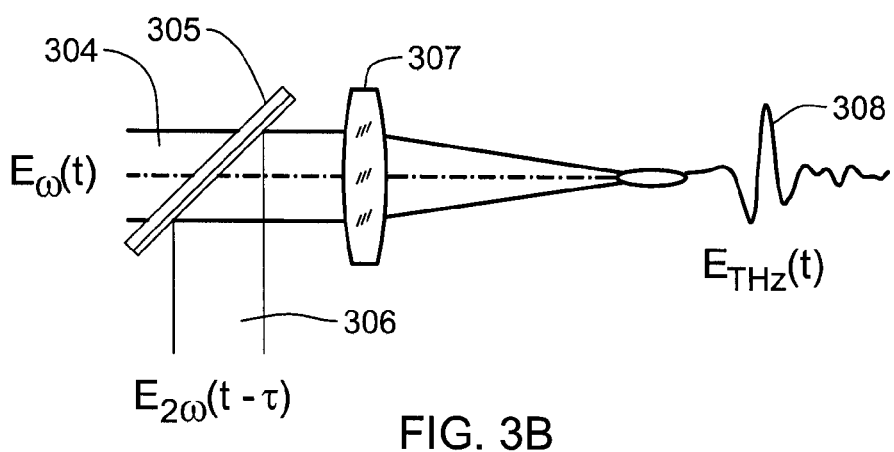
Figure 3C:
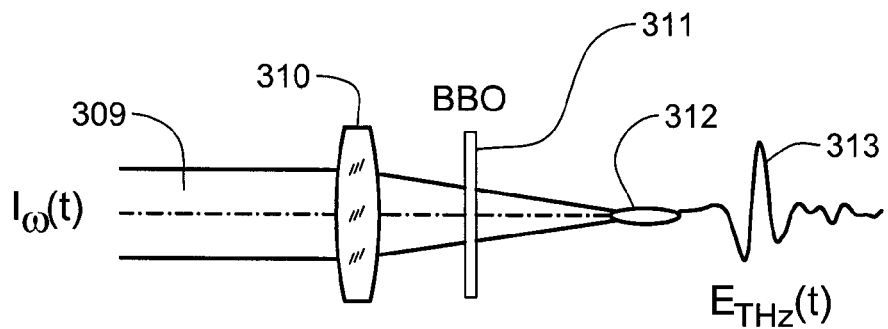

In one embodiment of a technique for remote analysis of an object, in accordance with an aspect of the present invention, several techniques to generate terahertz radiation in an ambient gas are provided. FIGS. 3A, 3B, and 3C illustrate three techniques to generate terahertz waves by using optical beams that may be utilized in the present invention. In the examples of FIGS. 3A, 3B, and 3C, a pulsed optical beam ionizes the ambient gas about the focal point of the beam, resulting in the generation of a volume of plasma. The ionized gas of the plasma radiates a broadband terahertz wave. FIG. 3A illustrates the generation of a terahertz wave 303 by focusing a pulsed laser beam 301, comprising predominantly one wavelength, with lens 302. The resultant terahertz wave has a broad bandwidth.

In FIG. 3B, dichroic mirror 305 combines fundamental optical beam 304 comprising a fundamental frequency of light and harmonic optical beam 306 comprising the second harmonic of the fundamental frequency. Harmonic optical beam 306 may have a phase delay $\tau$ relative to fundamental optical beam 304. Lens 307 focuses fundamental optical beam 304 and harmonic optical beam 306 in the same volume of ambient gas. A terahertz wave 308 induced by pulsed optical radiation comprising both fundamental and second harmonic frequencies may be more intense than the terahertz wave induced by optical radiation of a single wavelength as shown in FIG. 3A.

FIG. 3C illustrates another example of a technique to ionize ambient gas and inducing the ionized gas to emit a terahertz wave 313. In FIG. 3C, lens 310 focuses a pulsed optical beam 309 comprising a fundamental frequency. A nonlinear optical crystal 311, such as a β-barium borate (BBO) crystal, is placed between lens 310 and the focal point of the lens. The nonlinear optical crystal produces second harmonic waves. The residual fundamental waves and second harmonic waves produce an emitter plasma 312 and induce the emission of an intense terahertz wave therefrom. One of ordinary skill in the art would appreciate that additional optical processing components, such as a wave-plate, may be used in the techniques illustrated in FIGS. 3A, 3B, and 3C to further control the characteristics of the terahertz radiation generated.

In one example of the technique of FIG. 3A, the optical beam comprises 100 fs pulses of an 800 nm wavelength laser. In another example, the optical beam comprises 100 fs pulses of a 400 nm wavelength laser. In an example of the technique of FIG. 3B, the fundamental optical beam comprises an 800 nm wavelength, and the second harmonic optical beam comprises a 400 nm wavelength pulsed laser. In one example of the technique of FIG. 3C, the wavelength of fundamental optical beam incident to the lens is 800 nm.

When a terahertz wave is induced by a fundamental optical wave and its second harmonic, the magnitude of the electric field has been found to increase linearly with the energy of the fundamental optical wave once the energy of the fundamental optical wave exceeds a threshold. In contrast, it has been found that the electric field of the resulting terahertz wave increases approximately with the square root of the energy of the second harmonic optical beam once the energy of the fundamental optical wave exceeds a threshold. It has been observed that this energy threshold is very close to the energy threshold for ionizing air.

Measurements of the polarizations of terahertz pulses induced by one-wavelength optical pulses of 800 nm or 400 nm indicate that the polarizations of the resultant terahertz pulses are almost homogenous in directions perpendicular to the direction of pulse propagation. Also, the polarization of the induced terahertz pulses differed by less than 20 percent from the polarization of S polarized or P polarized optical excitation pulses.

It was also found that the electric field strength of a terahertz wave induced by a fundamental optical pulse and a second-harmonic optical pulse may be changed by controlling the polarization, intensity, and relative phase of the fundamental and second harmonic optical excitation pulses.

In another aspect of the present invention, an ionized ambient gas is utilized as a sensor for detecting terahertz radiation. One example of an ambient gas that may be utilized is air. Using air as a terahertz wave sensor advantageously provides flexibility in selecting a sensing location because air surrounds targeted objects to be analyzed in many environments of interest. Similar to the generation of a terahertz wave in the air by exploiting the third order nonlinear susceptibility of ionized air, terahertz waves are detected in ionized air with a third order nonlinear optical process. As will be appreciated by one of ordinary skill in the art, there are several possible techniques to provide a third order nonlinear optical process in air. The optical probe pulse interacts with the incident terahertz wave in a sensor plasma comprising air ionized by the optical probe pulse. The resultant optical pulse comprises optical radiation at the second harmonic of the fundamental frequency of the probe pulse. The measurement of the polarization rotation of optical radiation is known, and it provides a sensitive indirect detection technique for the terahertz waves by measuring the polarization change.

In another embodiment, a nonlinear interaction of ionized air, incident terahertz waves and an optical probe pulse generates a second harmonic of the probe pulse, and this second harmonic optical radiation is detected. In this embodiment, the resultant second harmonic optical radiation, which is modulated by the incident terahertz wave, comprises frequencies that are different from the frequencies of the probe pulses. This technique advantageously makes it possible to detect weak sensor output signals because strong background interference from the probe beam may be readily quenched due to the difference in the frequencies of the probe beam and sensor output signal.

The expression below illustrates the proportional relationship of the electric field strength, $E_{2\omega}(t, \tau)$, of the resulting second harmonic optical radiation to the electric field of the incident terahertz wave and the electric field of the probe beam for incoherent detection:

$$E_{2\omega}(t, \tau) \propto E_{Terahertz}(t-\tau)E_\omega(t)E_\omega(t) = E_{Terahertz}(t-\tau)I_\omega(t),$$

where $E_{1o7}(t, \tau)$ is the electric field strength of the optical probe beam having a frequency $\omega$ and where $E_{Terahertz}(t-\tau)$ is the electric field strength of the incident terahertz wave. The electric field strength, $E_{2\omega}(t, \tau)$, of the second harmonic optical radiation emitted by the sensor plasma is also proportional to the intensity of the probe beam ($I_\omega(t)$) because the square of the electric field $E_\omega(t)$ of the optical probe beam is proportional to its intensity. As illustrated by the above expression, two fundamental-frequency optical photons and one terahertz photon interact in the sensor plasma to produce a second harmonic photon. The time-resolved second harmonic optical intensity is detected to obtain the information carried by the incident terahertz wave. From the expression $E_{2\omega}(t) \propto E_{Terahertz}(t-\tau)I_\omega(t)$, it is apparent that the intensity of the second harmonic $I_{2\omega}(t)$ emitted by the sensor plasma in response to the incident probe beam and terahertz wave is proportional to the square of the intensity of the optical probe beam; that is, $I_{2\omega}(t) \propto I_{Terahertz}(t-\tau)I_\omega^2(t)$, where $I_{Terahertz}(t-\tau)$ is the intensity of the incident terahertz wave. This indicates that a strong probe beam, having fundamental frequency $\omega$, may greatly improve the detection of a weak terahertz wave by increasing the intensity of the second harmonic optical radiation emitted by the sensor plasma.

Figure 4:
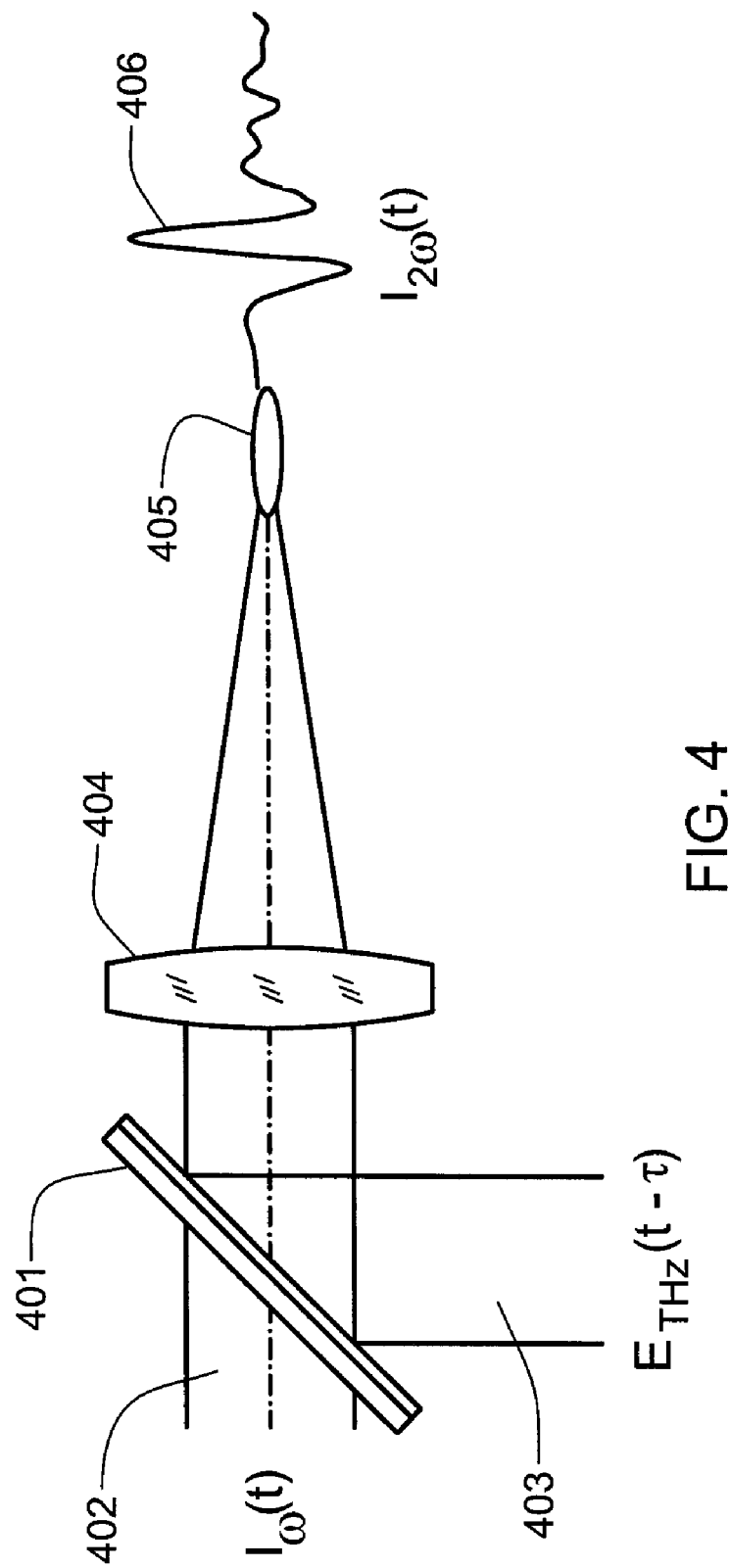
FIG. 4 illustrates one embodiment of a technique to detect terahertz radiation using a gas plasma as a sensor, in accordance with an aspect of the present invention.

FIG. 4 illustrates one embodiment of a technique for detection of terahertz radiation using air plasma as a sensor, in accordance with an aspect of the present invention. In this embodiment, dichroic mirror 401 combines optical probe beam 402 and terahertz wave 403 by transmitting the optical probe beam to lens 404 and reflecting the terahertz wave onto lens 404. Lens 404 focuses the incident optical probe beam and terahertz wave in an ambient gas. The focused optical probe beam ionizes the ambient gas in a volume about the lens's focal point to produce sensor plasma 405. Optical probe beam 402 and terahertz wave 403 are focused in sensor plasma 405. As a result of an interaction of the optical probe beam and terahertz wave in sensor plasma 405, sensor plasma 405 emits resultant optical radiation 406, comprising the second harmonic frequency of a frequency of the probe beam.

In another embodiment, a technique for coherent detection of terahertz radiation is utilized. In this embodiment, terahertz radiation to be detected is mixed nonlinearly with a probe beam that is derived from the same pump beam that induced the terahertz radiation. As a result, the time delays of the optical probe beam and terahertz radiation are correlated. Also, a strong fundamental probe beam creates a second harmonic background. Under these conditions, the second harmonic optical radiation emitted as a result of nonlinear interaction of the optical probe beam and incident terahertz radiation in the sensor plasma has an intensity $I_{2\omega}$ that may be characterized by the expression below, which illustrates the proportional relationship of the intensity of the resulting second harmonic optical radiation, $I_{2\omega}(t, \tau)$, to the electric field of the incident terahertz wave and the square of the intensity of the probe beam for coherent detection:

$$I_{2\omega} \propto (I_\omega)^2 E_{Terahertz}$$

where $I_\omega$ is the intensity of the optical probe beam having a frequency $\omega$ and where $E_{Terahertz}$ is the magnitude of the electric field of the incident terahertz wave. The intensity $I_{2\omega}$ of the second harmonic optical radiation output by the sensor plasma is proportional to the square of the intensity of the probe beam. The intensity $I_{2\omega}$ of the second harmonic optical radiation output by the sensor plasma is also proportional to the magnitude of the electric field of the incident terahertz wave. Experimental measurements indicate that coherent detection is feasible and that the intensity of the optical radiation emitted by the sensor plasma is related to the probe beam and incident terahertz radiation as shown in the expression above.

In one embodiment of a technique for coherent detection of terahertz radiation a photomultiplier detector is used to detect the optical radiation emitted as a result of the interaction of the optical probe beam and terahertz wave in the sensor plasma. In another embodiment of a technique for coherent detection of terahertz radiation, a photodiode was utilized to detect the optical radiation emitted by the sensor plasma.

Since it has been observed in experiments that the lifetime of laser-induced air plasma may exceed 150 picoseconds, the same air plasma may be used as an emitter plasma for terahertz wave generation and subsequently as a sensor plasma for the terahertz wave detection in an embodiment of a technique to analyze a remotely-located object. It is possible to send a relatively weak probe beam to the same plasma used as a terahertz wave emitter to take advantage of the large resonance third-order nonlinearity, which was produced by the optical pump beam generating the terahertz wave, to detect a terahertz wave incident to the plasma.

Figure 5:
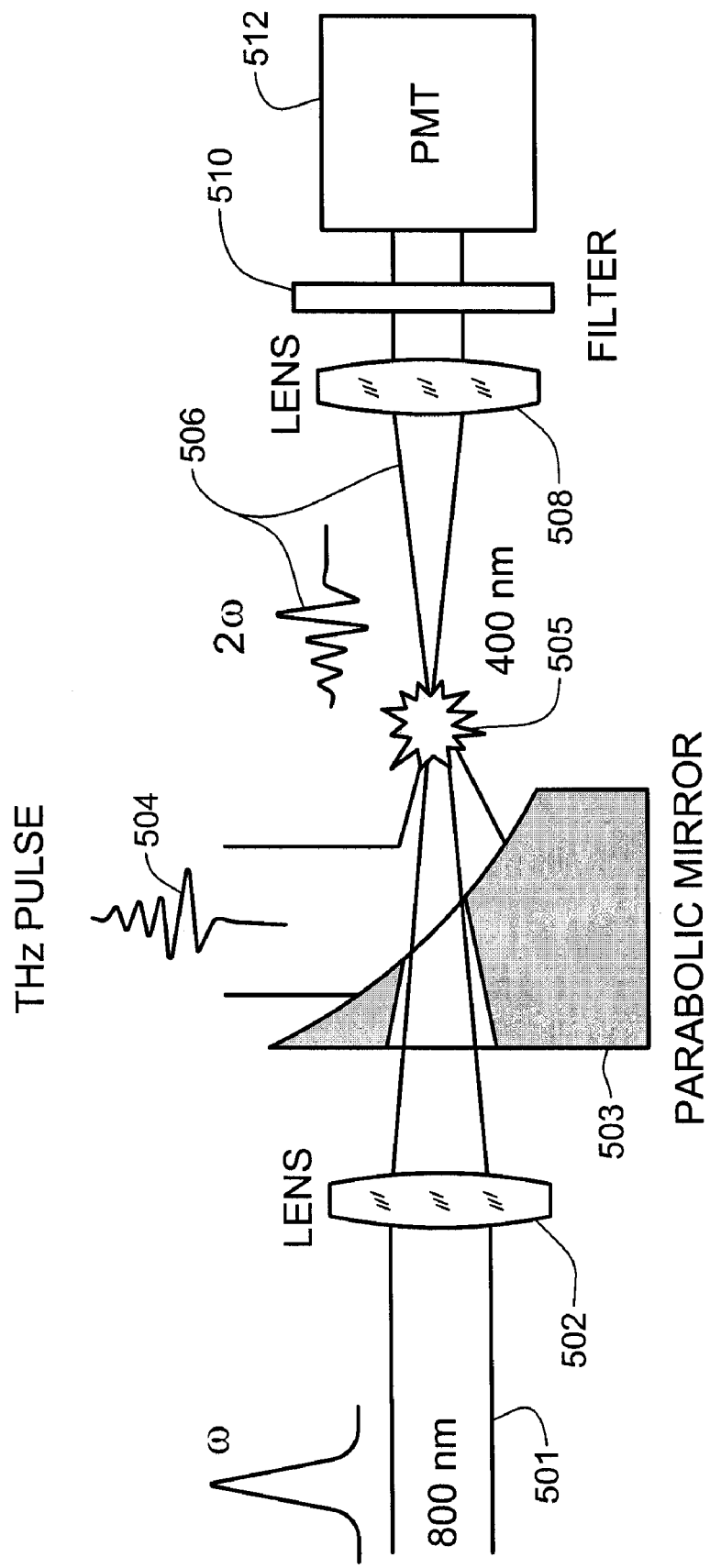
FIG. 5 illustrates one embodiment of a system for detecting terahertz radiation using an ionized gas as a sensor, in accordance with an aspect of the present invention.

FIG. 5 illustrates one embodiment of a system for detecting terahertz radiation. This embodiment comprises a source of optical probe beam 501 and lens 502 for inducing sensor plasma 505, and a parabolic mirror 503. In this embodiment, a second harmonic optical beam 506 is emitted as a result of an interaction of optical probe beam 501 and terahertz radiation 504 in the sensor plasma. Lens 502 focuses optical probe beam 501. Parabolic mirror 503 has an opening hole that passes the focused optical probe beam. The parabolic mirror also focuses terahertz radiation in a volume of ambient gas excited by the focused optical probe beam. Second harmonic optical beam 506, which is modulated by information carried by the incident terahertz radiation, is transmitted through lens 508 and filter 510 and is detected by photomultiplier detector 512. Lens 508 collimates second harmonic optical beam 506 to provide a stronger signal. Filter 510 attenuates optical background radiation, including the optical probe beam, before photomultiplier detector 512 detects second harmonic optical beam 506. In an exemplary embodiment, the optical probe beam comprises pulses of 800 nm wavelength radiation, and the resulting second harmonic optical beam comprises pulses of 400 nm wavelength radiation.

Figure 6A:
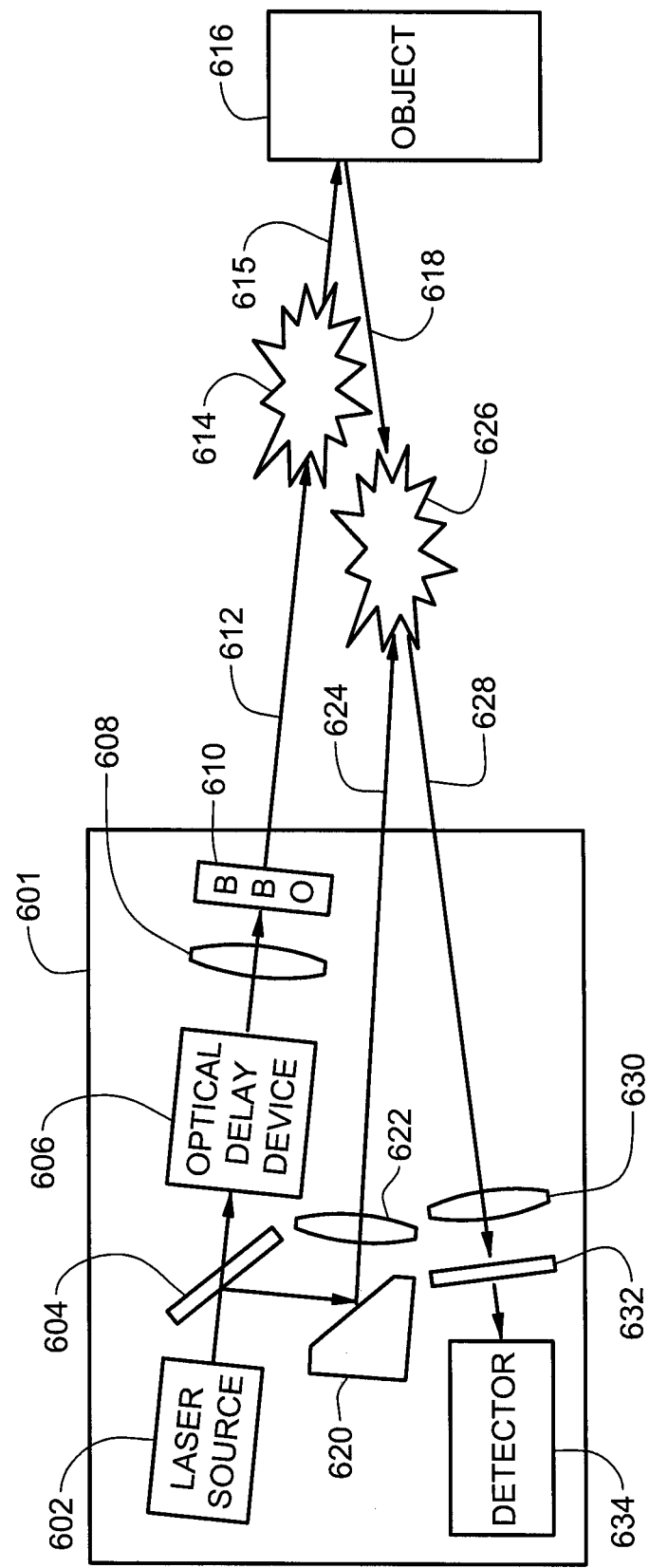
FIGS. 6A and 6B illustrate an embodiment of a system for analyzing a remotely-located object, in accordance with an aspect of the present invention.
Figure 6B:
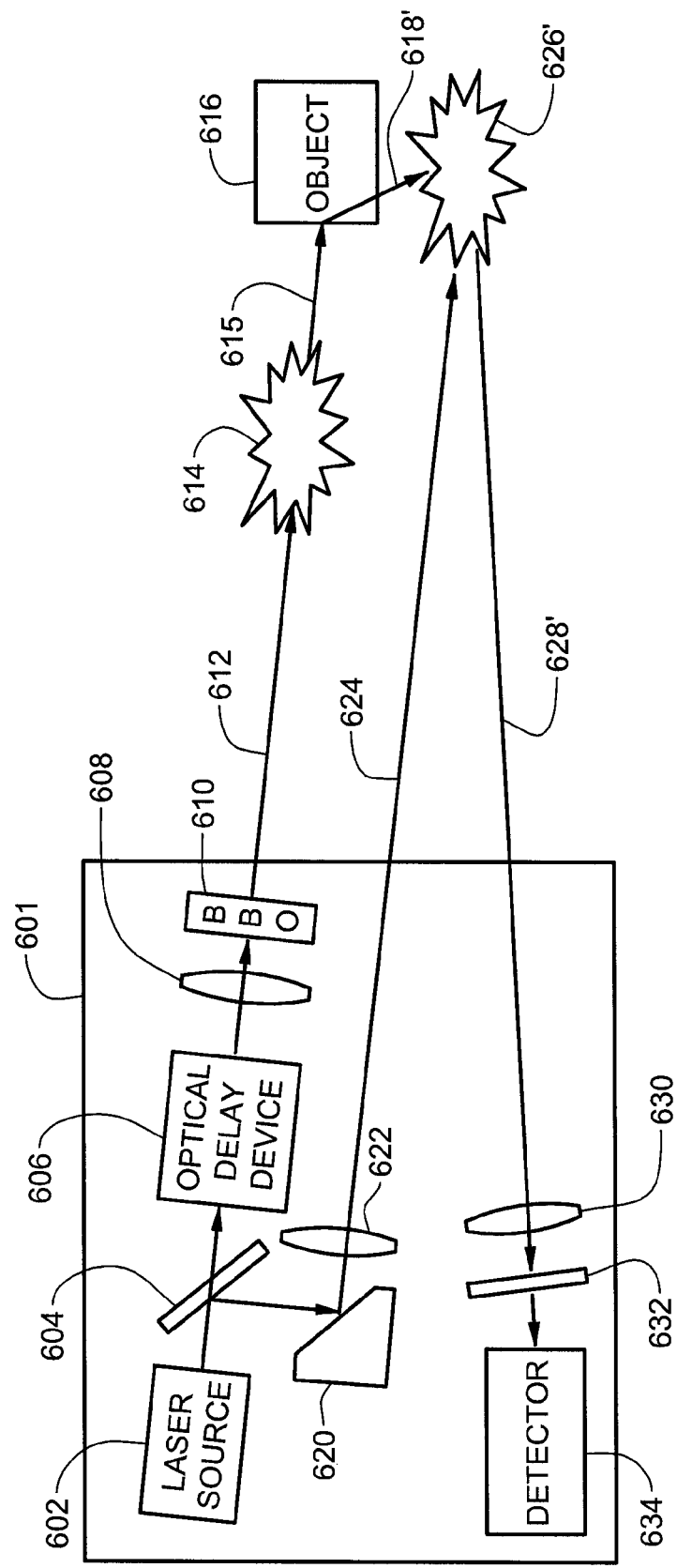

FIGS. 6A and 6B illustrate one embodiment of a system 601 for analyzing a remotely-located object, in accordance with another aspect of the present invention. This system comprises a source of an optical pump beam, means for focusing the optical pump beam, a source of an optical probe beam, means for focusing an optical probe beam that is modulated with a signature of a targeted object that was imposed onto detected terahertz radiation by the object, and an optical detector. The optical pump beam induces an ionized gas to generate terahertz radiation that is directed to an object to be analyzed. The terahertz radiation incident to the object interacts with the object, and the object reflects (as in FIG. 6A) or scatters (as in FIG. 6B) at least a portion of the incident terahertz radiation. A source of an optical probe beam provides a focused optical probe beam for ionizing a volume of ambient gas to produce a sensor plasma. The sensor plasma emits a resultant optical beam as a result of an interaction of the optical probe beam and the terahertz radiation reflected or scattered by the object. The resultant optical beam emitted by the sensor plasma is detected by an optical detector such as a photomultiplier detector or a photodiode.

In the embodiment of FIGS. 6A and 6B, the source of an optical pump beam comprises laser source 602, beamsplitter 604, optical delay device 606, and lens 608. One example of optical delay device 606 comprises a series of mirrors arranged to increase the length of the optical radiation's propagation path. Lens 608 focuses an optical beam provided by the laser source to produce optical pump beam 612. In this embodiment, optical pump beam 612 ionizes the ambient gas in a volume to produce emitter plasma 614. The interaction of optical pump beam 612 with emitter plasma 614 induces the emitter plasma to emit terahertz radiation 615 propagating toward an object to be analyzed 616. In response to the incident terahertz radiation, the object reflects (as in FIG. 6A) or scatters (as in FIG. 6B) a portion of the incident terahertz radiation to produce reflected terahertz radiation 618 or scattered terahertz radiation 618'.

The system of FIGS. 6A and 6B also provides optical probe beam 624, which ionizes the ambient gas in a volume to produce sensor plasma 626. Optical probe beam 624 is produced by beamsplitter 604, mirror 620, and lens 622. Beamsplitter 604 directs a portion of the optical radiation from laser source 602 to mirror 620. Mirror 620 directs incident optical radiation from the beamsplitter to lens 622, which focuses the optical radiation from mirror 620 to provide optical probe beam 624. As a result of the interaction of optical probe beam 624 and reflected or scattered terahertz radiation 618 in sensor plasma 626, a resultant optical radiation 628 is emitted from the sensor plasma. Resultant optical radiation 628, comprising, for example, a second harmonic frequency of the optical probe beam's fundamental frequency, is concentrated by lens 630 and filtered by filter 632 to attenuate background optical radiation. Optical detector 634 detects a second harmonic component of resultant optical radiation 628 that is passed by filter 632. Optical detector 634 may comprise a photomultiplier detector, for example, or a photodiode, as another example.

In the embodiment of FIGS. 6A and 6B, the optical pump beam source may also include a nonlinear optical crystal 610, such as a β-barium borate (BBO) crystal, to induce the emitter plasma to emit stronger terahertz radiation.

Figure 6C:
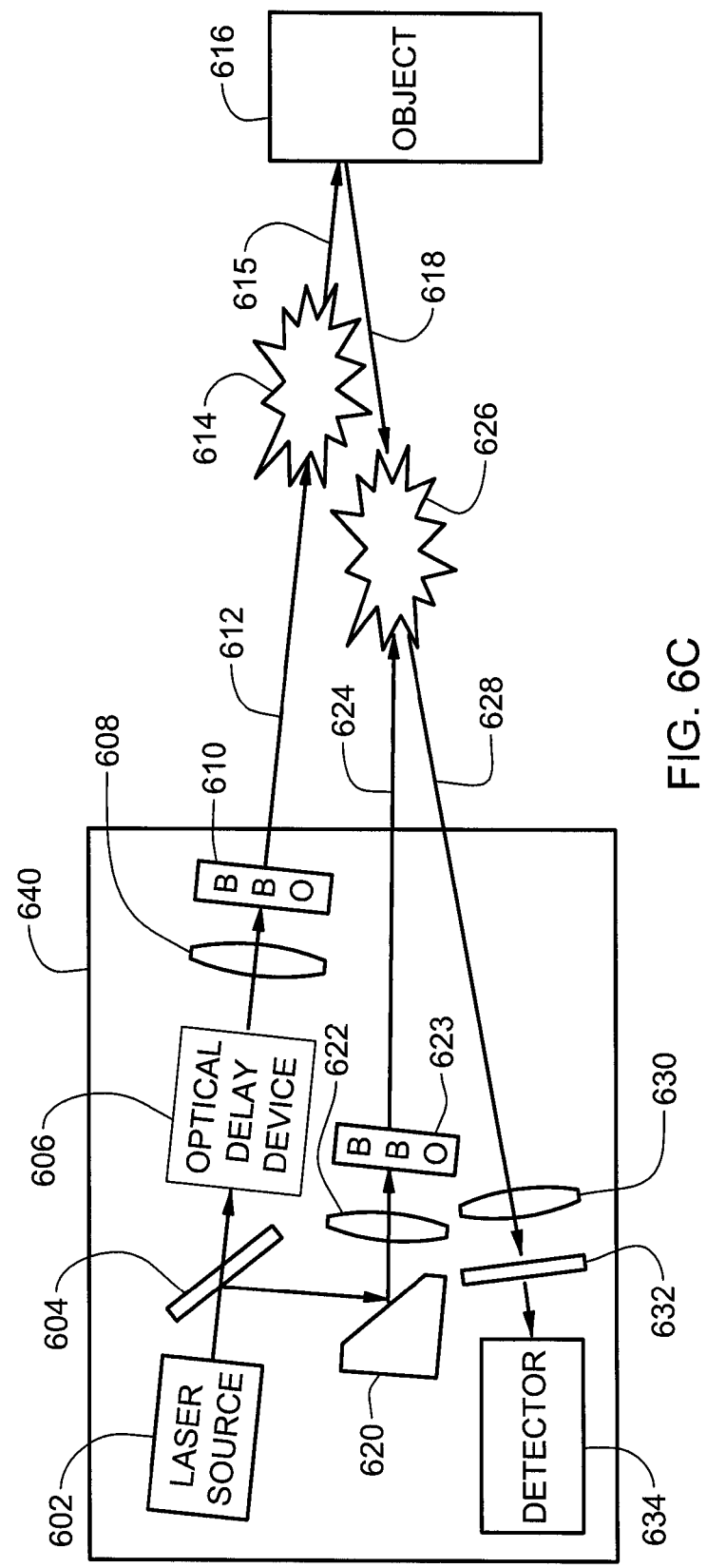
FIGS. 6C and 6D illustrate another embodiment of a system for analyzing a remotely-located object, in accordance with an aspect of the present invention.
Figure 6D:
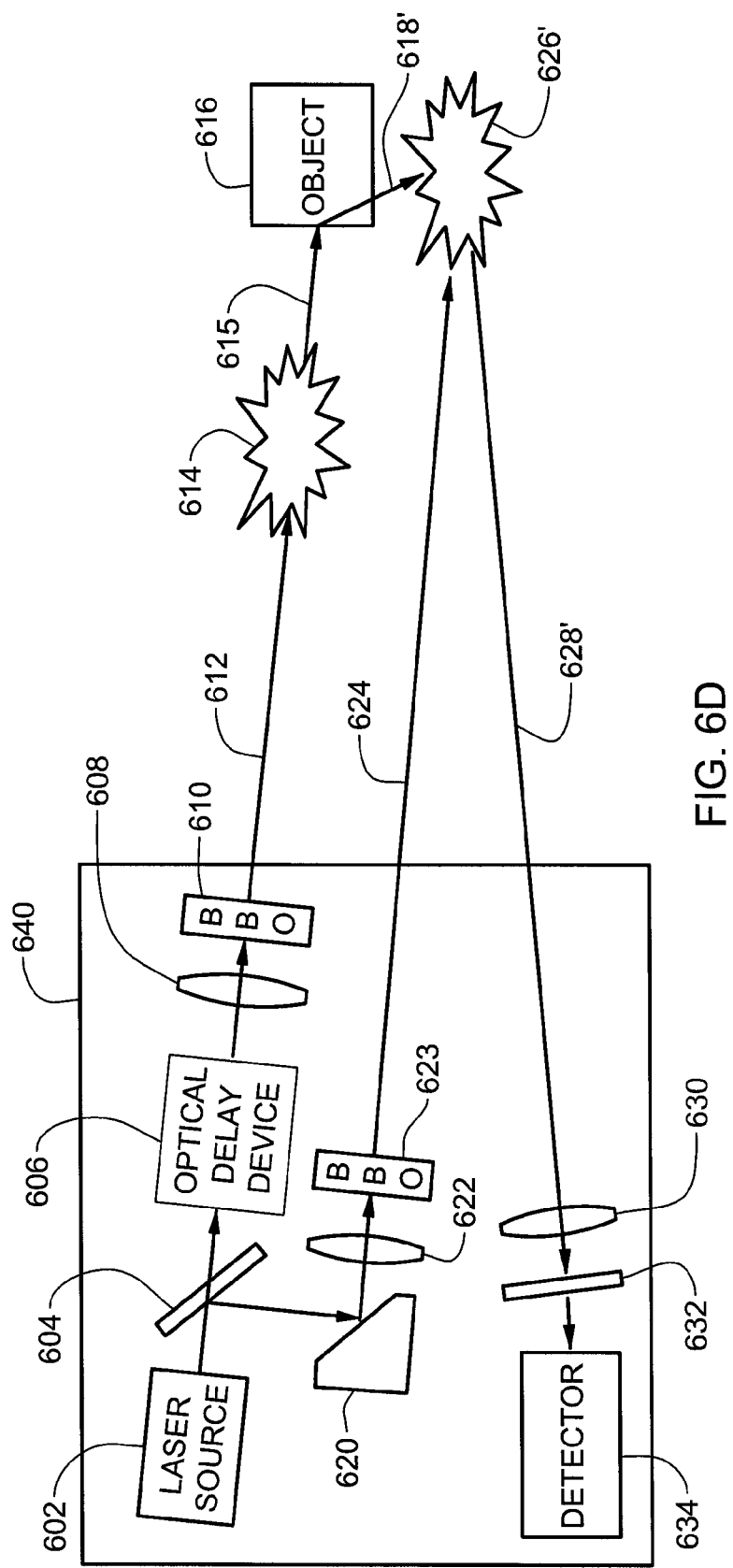

FIGS. 6C and 6D illustrate another embodiment of a system 640 for analyzing a remotely-located object, in accordance with an aspect of the present invention. System 640 of FIGS. 6C and 6D includes nonlinear optical crystal 623 added to system 601 of FIGS. 6A and 6B. In this embodiment, nonlinear optical crystal 623 is placed after lens 622 in the optical processing path that produces optical probe beam 624. Optical probe beam 624 produced by nonlinear optical crystal 623 comprises a fundamental frequency component, having the frequency of the optical radiation output by the laser source, and a second harmonic component. As a result of the interaction of the a fundamental frequency component of optical probe beam and its second harmonic with the incident terahertz radiation in the sensor plasma, resultant optical radiation, comprising the second harmonic frequency, is emitted by the sensor plasma. This resultant optical radiation is modulated by the object's signature carried by the reflected terahertz radiation.

Figure 6E:
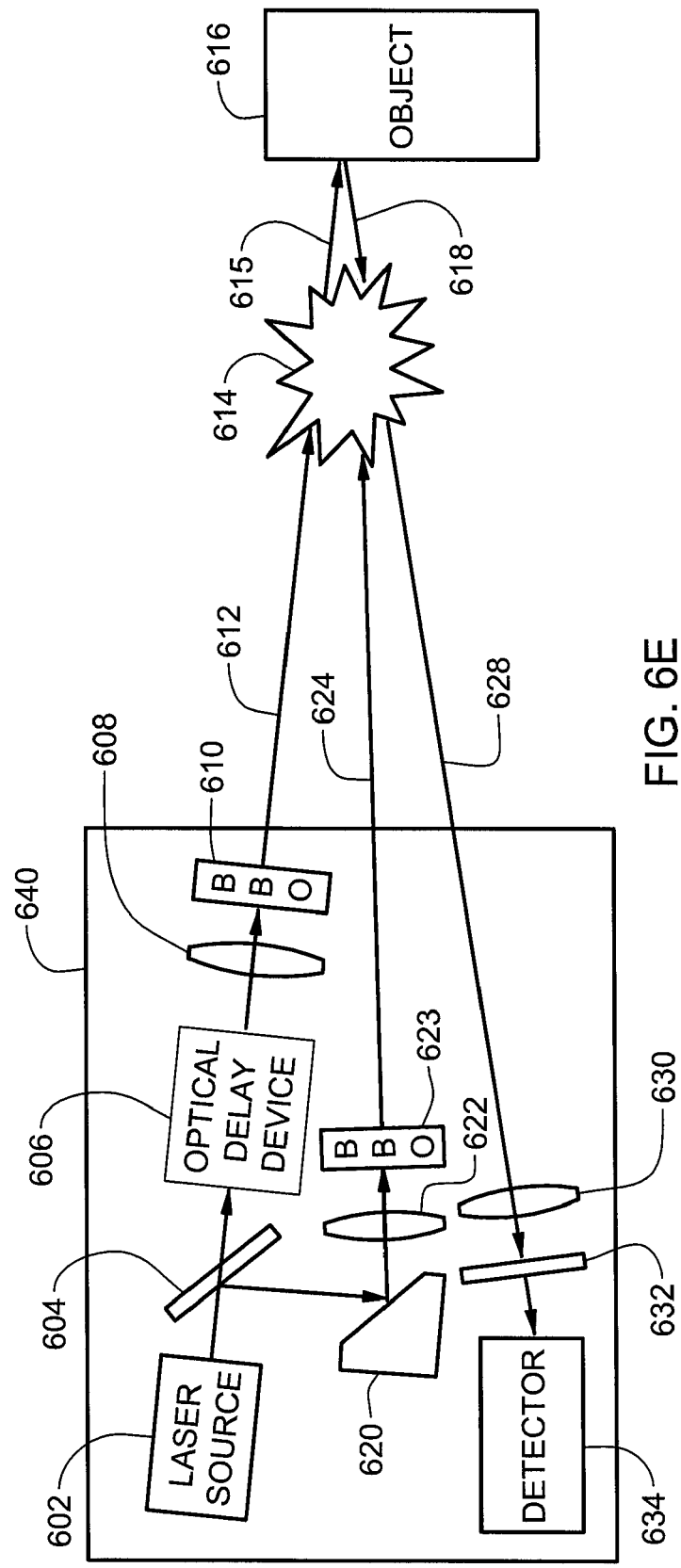
FIG. 6E illustrates an embodiment of a system for analyzing a remotely-located object wherein the same plasma is used as an emitter and sensor of terahertz radiation, in accordance with an aspect of the present invention.

FIG. 6E illustrates an embodiment of a system for analyzing a remotely-located object wherein the same plasma is used as an emitter and sensor of terahertz radiation, in accordance with an aspect of the present invention. As in the embodiment of FIG. 6C, optical pump beam 612 ionizes the ambient gas in a volume to produce emitter plasma 614. Emitter plasma 614 emits terahertz radiation 615 propagating toward an object to be analyzed 616. In response to the incident terahertz radiation, the object reflects a portion of the incident terahertz radiation to produce reflected terahertz radiation 618. In the embodiment of FIG. 6E, system 640 for analyzing a remotely-located object focuses optical probe beam 624 in emitter plasma 614, and the interaction of the optical probe beam 624 with reflected terahertz radiation 618 in the emitter plasma 614 produces resultant optical radiation 628. That is, the same plasma that emits terahertz radiation directed toward the targeted object is also used to sense the terahertz radiation that results from an interaction of terahertz radiation 615 with the object to be analyzed 616. Optical detector 634 detects a component of resultant optical radiation 628 that is passed by filter 632. For example, the detected component may be a second harmonic of the optical probe beam 624.

Figure 7A:
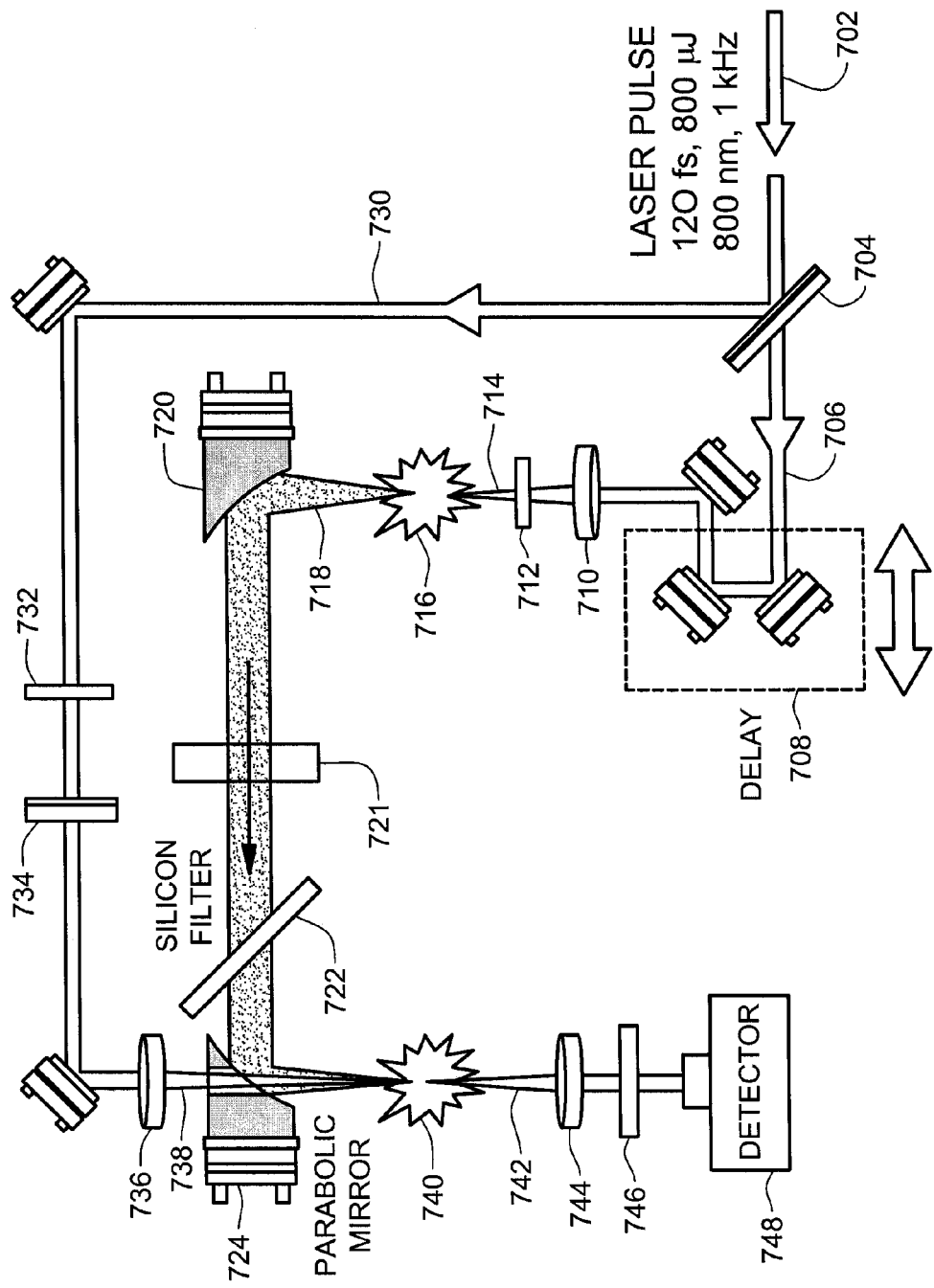
FIG. 7A illustrates an embodiment of a system that utilizes optically-induced ionized gas to emit and detect terahertz radiation to analyze objects, in accordance with an aspect of the present invention, wherein a terahertz wave transmitted through a targeted object is detected.
Figure 7B:
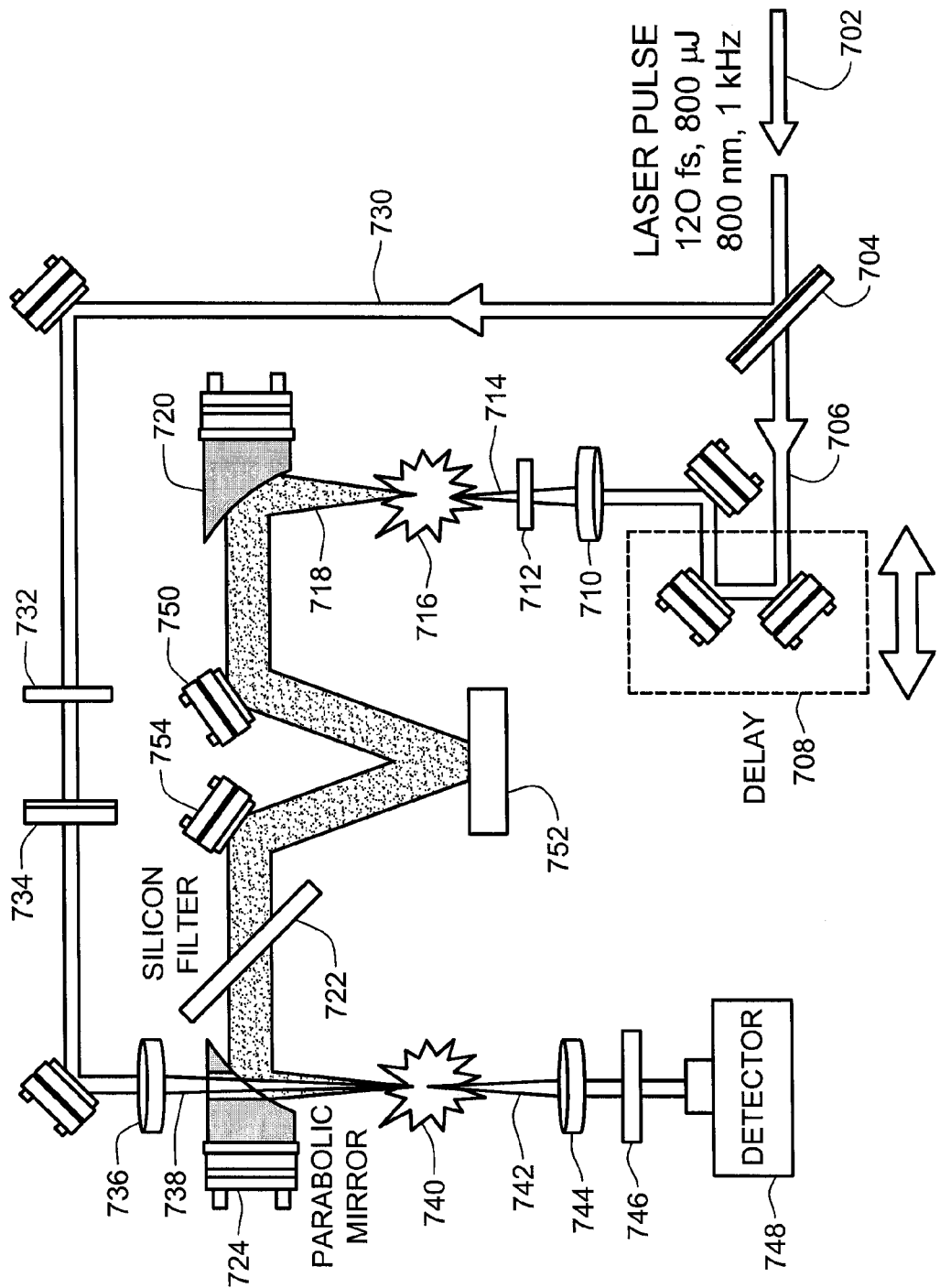
FIG. 7B illustrates an embodiment of a system that utilizes optically-induced ionized gas to emit and detect terahertz radiation to analyze objects, in accordance with an aspect of the present invention, wherein a terahertz wave reflected by a targeted object is detected.

FIGS. 7A and 7B illustrate embodiments of a system that utilizes optically-induced ionized gas to emit and detect terahertz radiation, in accordance with an aspect of the present invention. In FIG. 7A, a terahertz wave transmitted through the targeted object is measured, and, in FIG. 7B, a terahertz wave reflected by the object is measured. A laser source comprising a Ti:sapphire amplifier generates laser beam 702 comprising optical pulses. For example, the Ti:sapphire amplifier generates 120 fs optical pulses at a repetition rate of 1 kHz with a central wavelength at 800 nm. In one example of this embodiment, the optical pulses of laser beam 702 have energies of 800 µJ or more. Laser beam 702 is split into two beams by a beamsplitter 704. One beam, fundamental pump beam 706, is used to generate terahertz waves, and the other beam, probe beam 730, is used to detect the terahertz waves. Fundamental pump beam 706 is delayed by optical delay 708 comprising a plurality of mirrors. Delayed fundamental pump beam 706 is focused by lens 710. The delayed and focused fundamental pump beam is processed by a nonlinear optical device 712 to produce a composite optical pump beam 714 comprising the fundamental pump beam, having frequency $\omega$, and its second harmonic, having frequency $2\omega$. In one embodiment, the nonlinear optical device comprises a 100-mm thick type-I β barium borate (BBO) crystal. The composite pump beam is focused in an ambient gas (for example, air) to produce emitter plasma 716. Composite pump beam 714 induces emitter plasma 716 to emit an intense, highly directional, broadband terahertz wave 718, which is generated through a four-wave-mixing optical process. In FIG. 7A, terahertz wave 718 is collimated by a parabolic mirror 720, transmitted through targeted object 721, and focused by refocusing mirror 724. In one embodiment, collimating mirror 720 has a 76.2-mm diameter with a 101.6-mm effective focal length, and refocusing mirror 724 has a 50.8-mm diameter and a 50.8-mm focal length. In FIG. 7B terahertz wave 718 is collimated by a parabolic mirror 720 and directed by metal mirrors 750 and 754, and targeted object 752 reflects the terahertz wave. In both embodiments, the terahertz wave is focused by a second parabolic mirror, refocusing mirror 724, and refocusing mirror 724 has a hole to allow focused probe beam 738 to pass through. Refocusing mirror 724 has a hole to allow focused probe beam 738 to pass through. Filter 722 transmits terahertz wave 718 and blocks the residual 800 nm and 400 nm beams. For example, filter 722 may comprise a high-resistivity silicon wafer.

Half-wavelength waveplate 732 may be utilized to control the polarization of probe beam 730, and filter 734 may be utilized to further process the probe beam. Lens 736 focuses the probe beam in a volume of an ambient gas in which sensor plasma 740 is produced. Terahertz wave 718 is detected by the reciprocal process of its generation in which a second harmonic optical signal 742 is produced by mixing focused probe beam 738 and the incident terahertz field. A time-resolved measurement of second harmonic optical signal 742 provides coherent detection of the amplitude and phase of terahertz field 718.

In examples of the embodiments illustrated in FIGS. 7A and 7B, the terahertz wave and the probe beam are focused at the same point in sensor plasma 740, with estimated focal spots of about 0.8 mm and 24 µm in diameter, respectively. The terahertz-field-induced-second-harmonic optical signal is detected by a photomultiplier tube 748. Optionally, detection of second harmonic optical signal 742 may be improved by focusing the second harmonic optical signal with lens 744 and employing filter 746 to attenuate background optical radiation, including radiation at the optical probe beam's fundamental frequency. In the embodiments of FIGS. 7A and 7B, a unipolar waveform was detected when the probe beam intensity was less than about $1.8\times10^{14}$ W/cm$^2$. Above this intensity level, the detected waveform begins to change, and above approximately $5.5\times10^{14}$ W/cm$^2$ the measured second harmonic waveform is bipolar and coherent detection is obtained.

Figure 7C:
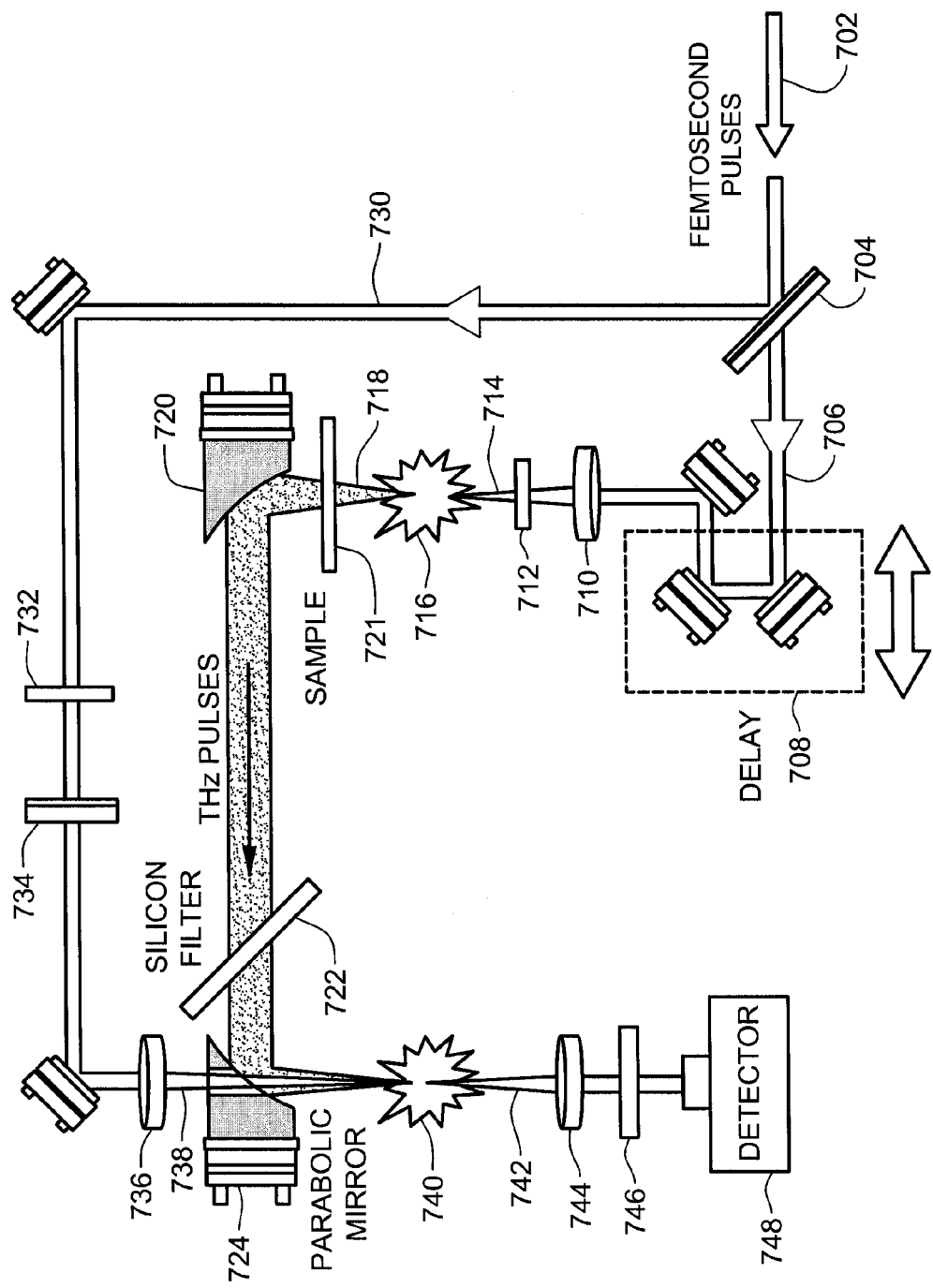
FIG. 7C illustrates another embodiment of a system that utilizes optically-induced ionized gas to emit and detect terahertz radiation to analyze objects, in accordance with an aspect of the present invention, wherein a terahertz wave transmitted through a targeted object is detected.

FIG. 7C illustrates another embodiment of a system that utilizes optically-induced ionized gas to emit and detect terahertz radiation to analyze objects, in accordance with an aspect of the present invention, wherein a terahertz wave transmitted through a targeted object is detected. The embodiment is similar to the embodiment illustrated in FIG. 7A. The embodiment of FIG. 7C differs from the embodiment of FIG. 7A in that targeted object 721 is positioned between emitter plasma 716 and parabolic mirror 720 rather than between parabolic mirror 720 and filter 722.

Figure 8A:
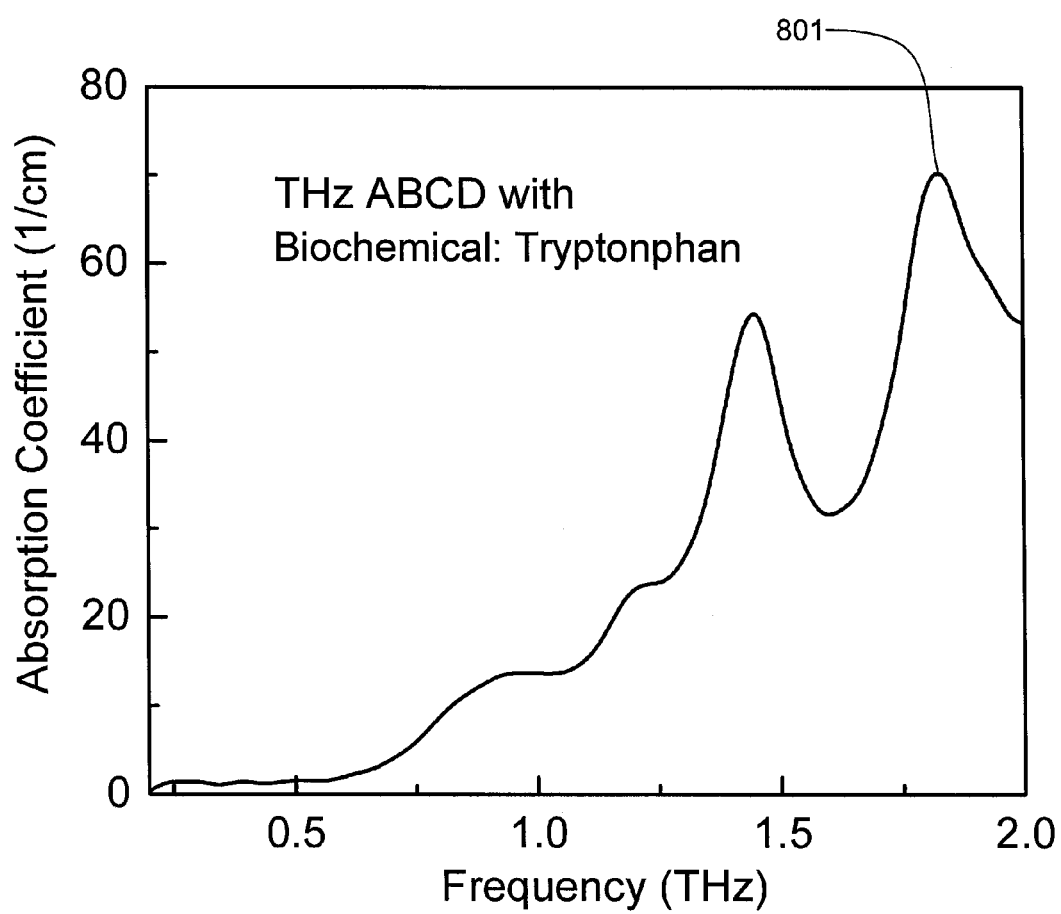
FIG. 8A illustrates a plot of the measured absorption coefficient of tryptonphan obtained using the embodiment of FIG. 7C, in accordance with the present invention.

FIG. 8A illustrates a plot 801 of the measured absorption coefficient of the biochemical tryptonphan obtained using the embodiment of FIG. 7C, in accordance with the present invention. In this test, targeted object 721 of FIG. 7C comprised a sample of tryptonphan. The optical signal detected by photomultiplier tube 748 was analyzed to obtain the measured absorption coefficient of tryptonphan for a range of frequencies from about 0.25 THz to 2 THz.

Figure 8B:
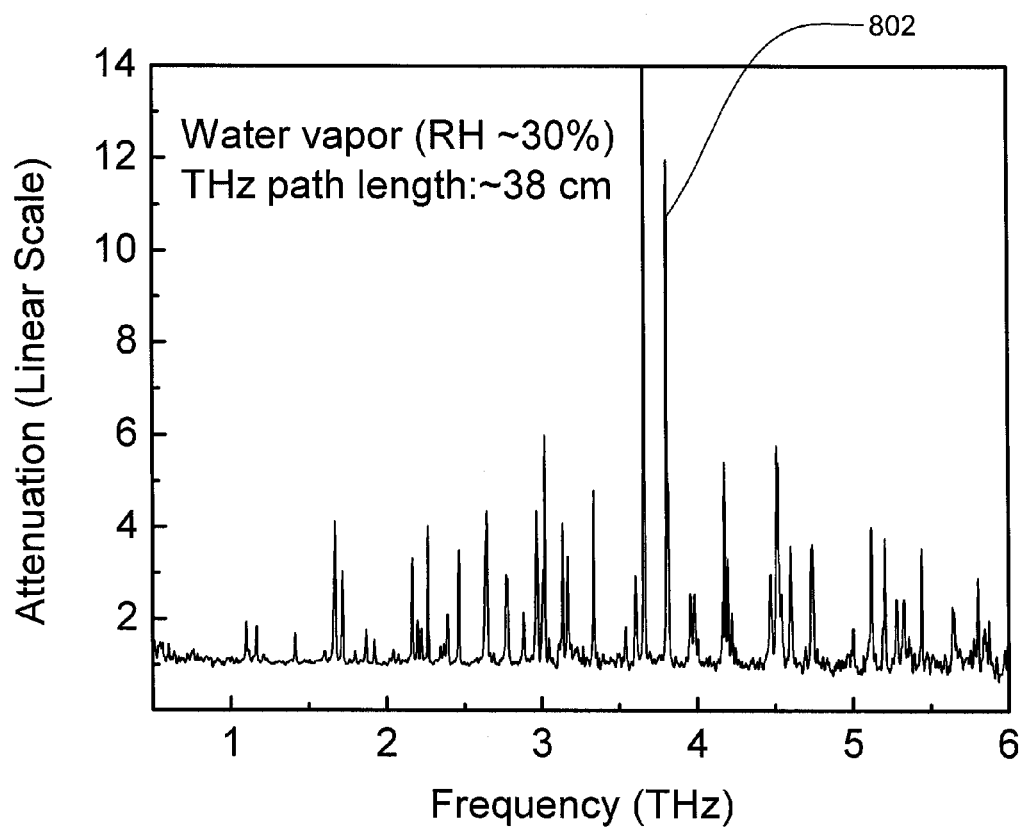
FIG. 8B illustrates a plot of the measured attenuation of water vapor at 30 percent relative humidity and at a room temperature as a function of frequency obtained using the embodiment of FIG. 7C, in accordance with the present invention.

FIG. 8B illustrates a plot 802 of the measured attenuation of terahertz radiation by water vapor at 30 percent relative humidity around room temperature as function of frequency obtained using the embodiment of FIG. 7C, in accordance with the present invention. In this test, targeted object 721 comprised a sample of water vapor having a path length of approximately 38 cm. The optical signal detected by photomultiplier tube 748 was analyzed to obtain the measured attenuation of terahertz radiation by water vapor over a 38 cm path for a range of frequencies from about 0.5 THz to 6 THz.

Figure 9A:
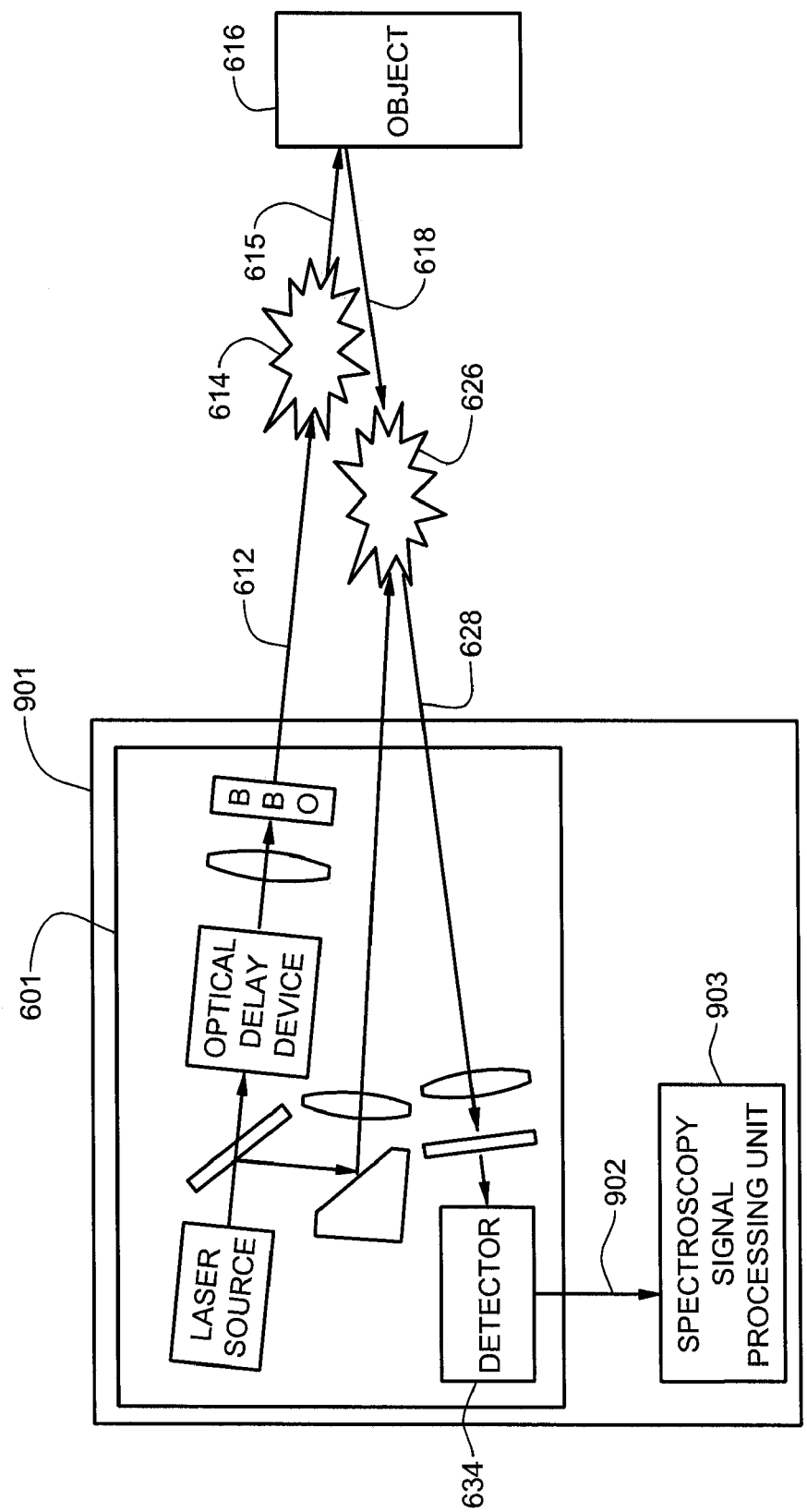
FIG. 9A illustrates an embodiment of a system for analyzing a remotely-located object that provides spectroscopy analysis, in accordance with an aspect of the present invention.

FIG. 9A illustrates an embodiment of a system 901 for analyzing a remotely-located object that provides spectroscopy analysis, in accordance with an aspect of the present invention. System 901 includes system 601 of FIG. 6A and further comprises spectroscopy signal processing unit 903 for analyzing signal 902, which is provided by optical detector 634 in response to the detected component of resultant optical radiation 628.

Figure 9B:
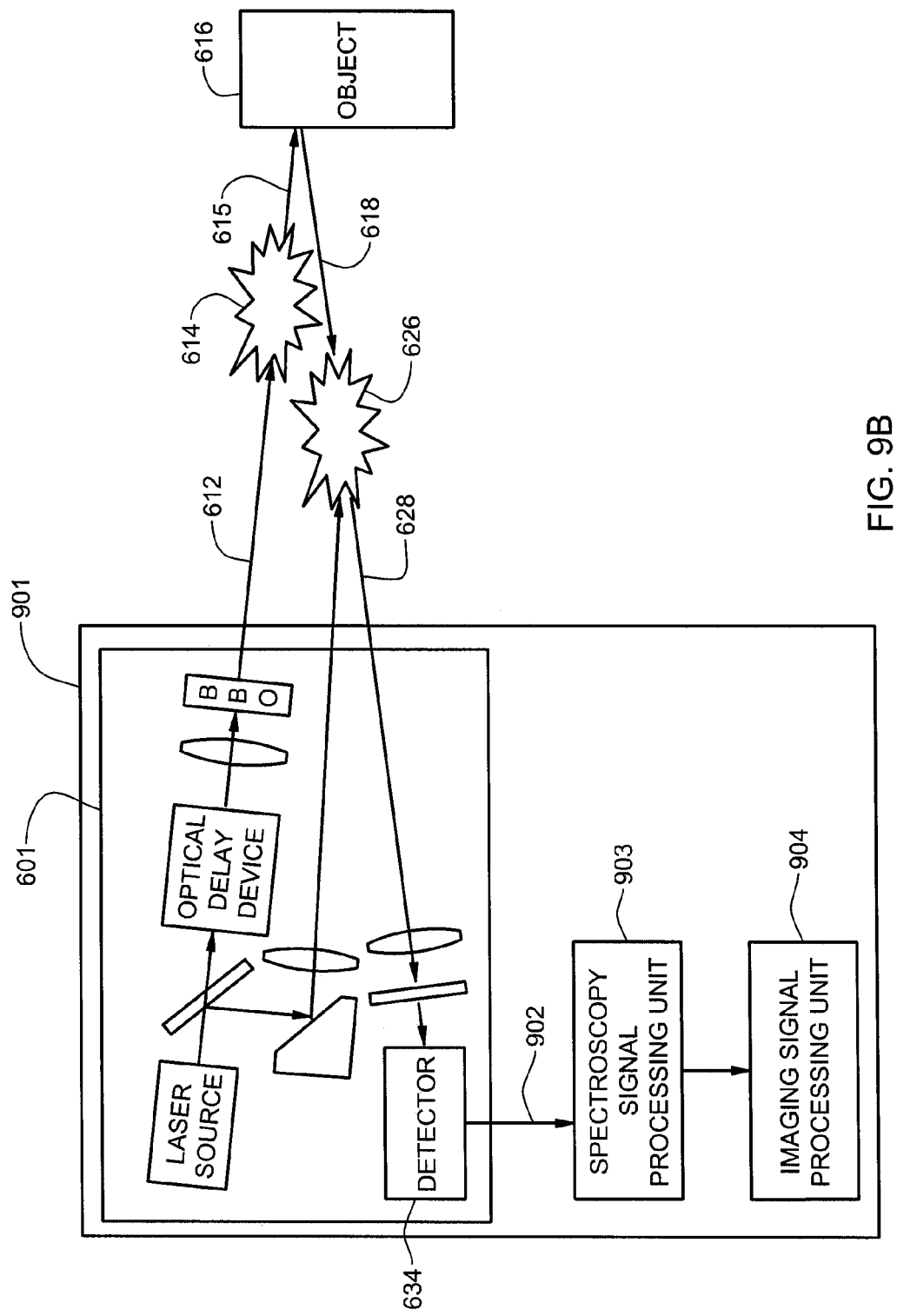
FIG. 9B illustrates an embodiment of a system for analyzing a remotely-located object that provides spectroscopic imaging, in accordance with an aspect of the present invention.

FIG. 9B illustrates another embodiment of system 901 for analyzing a remotely-located object that provides spectroscopic imaging, in accordance with an aspect of the present invention. In this embodiment, system 901 additionally includes imaging signal processing unit 904, which is coupled to spectroscopy signal processing unit 903. Imaging signal processing unit 904 produces a spectroscopic image of the targeted object, or a feature thereof, from an output of spectroscopy signal processing unit 903. Spectroscopy signal processing unit 903 and imaging signal processing unit 904 may comprise programs of instructions that are executable on a computer, microprocessor, or digital signal processor (DSP) chip, for example.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. A method of detecting terahertz radiation comprising:
   ionizing a volume of an ambient gas to produce a sensor plasma by focusing an optical probe beam in the volume; and
   detecting an optical component of resultant radiation produced from an interaction of the focused optical probe beam and an incident terahertz wave in the sensor plasma.

2. The method of claim 1 further comprising focusing the terahertz wave in the sensor plasma.

3. The method of claim 1 wherein the detecting comprises focusing at least the optical component of the resultant radiation with means for optical focusing located a distance from the sensor plasma.

4. The method of claim 1 wherein the detecting further comprises attenuating a component of the resultant radiation, the component comprising a frequency of the optical probe beam.

5. The method of claim 1 wherein the optical probe beam comprises an optical radiation component having a fundamental frequency and a harmonic optical radiation component having a frequency that is harmonically related to the fundamental frequency.

6. A method of analyzing a remotely-located object comprising:
   inducing a volume of ionized ambient gas to emit pulsed terahertz radiation directed toward a targeted object by focusing an optical pump beam in the volume;
   ionizing another volume of an ambient gas to produce a sensor plasma by focusing an optical probe beam in the another volume; and
   detecting an optical component of resultant radiation produced from an interaction of the focused optical probe beam and an incident terahertz wave in the sensor plasma, the incident terahertz wave being produced by an interaction of the pulsed terahertz radiation with the targeted object.

7. The method of claim 6 further comprising focusing the incident terahertz wave in the sensor plasma.

8. The method of claim 6 wherein the detecting comprises focusing the optical component of the resultant radiation with means for optical focusing located a distance from the sensor plasma.

9. The method of claim 6 wherein the optical component of the resultant radiation comprises a harmonic of a fundamental frequency of the optical probe beam.

10. The method of claim 6 wherein the optical probe beam comprises at least one pulse of optical radiation.

11. The method of claim 6 wherein the targeted object comprises an explosive material or a biological agent or a chemical agent that is harmful to humans.

12. The method of claim 6 wherein the optical probe beam comprises an optical radiation component having a fundamental frequency and a harmonic optical radiation component having a frequency that is harmonically related to the fundamental frequency.

13. The method of claim 6 wherein the volume of ionized ambient gas is located more than thirty meters away from a source of the optical pump beam.

14. The method of claim 6 wherein the sensor plasma is located more than thirty meters away from a site where the optical component is detected.

15. The method of claim 6 wherein the detecting is performed more than thirty meters from the targeted object.

16. The method of claim 6 wherein the volume and the another volume overlap.

17. The method of claim 6 further comprising processing the optical component of resultant radiation detected by the detecting to produce spectroscopy analysis information.

18. The method of claim 17 further comprising producing a spectroscopy image from the spectroscopy analysis information.

19. A system for detecting terahertz radiation comprising:
   a source of an optical probe beam;
   means for focusing the optical probe beam to produce a focused optical probe beam that ionizes a volume of an ambient gas to produce a sensor plasma; and
   an optical detector for detecting an optical component of resultant radiation emitted from the sensor plasma as a result of an interaction, in the sensor plasma, of the focused optical probe beam and an incident terahertz wave.

20. The system of claim 19 further comprising a means for focusing the terahertz wave in the sensor plasma.

21. The system of claim 19 wherein the optical detector comprises means for focusing the optical component of the resultant radiation, the means for focusing the optical component being located a distance from the sensor plasma.

22. The system of claim 19 wherein the optical component of the resultant radiation comprises a harmonic of a fundamental frequency of the optical probe beam, and the optical detector further comprises an optical filter for attenuating a component of the resultant radiation comprising the fundamental frequency of the optical probe beam.

23. The system of claim 19 wherein the optical probe beam comprises at least one pulse of optical radiation.

24. The system of claim 19 wherein the terahertz wave comprises at least one pulse of terahertz radiation.

25. The system of claim 19 wherein the optical probe beam comprises an optical radiation component having a fundamental frequency and a harmonic optical radiation component having a frequency that is harmonically related to the fundamental frequency, and the system further comprises means for shifting a relative phase of the optical radiation component and the harmonic optical radiation component.

26. The system of claim 19 wherein the optical detector comprises a photomultiplier tube or a photodiode.

27. A system for analyzing a remotely-located object comprising:
   a source of an optical pump beam;
   means for focusing the optical pump beam to produce a focused optical pump beam that ionizes a volume of an ambient gas to produce an emitter plasma and induces an emission, from the emitter plasma, of pulsed terahertz radiation directed toward a targeted object;
   a source of an optical probe beam;
   another means for focusing the optical probe beam to produce a focused optical probe beam that ionizes another volume of the ambient gas to produce a sensor plasma; and
   an optical detector for detecting an optical component of resultant radiation emitted from the sensor plasma as a result of an interaction, in the sensor plasma, of the focused optical probe beam and a resultant terahertz wave, the resultant terahertz wave comprising terahertz radiation reflected, scattered, or transmitted by the targeted object in response to an incidence of the pulsed terahertz radiation at the targeted object.

28. The system of claim 27 further comprising means for focusing the resultant terahertz wave in the sensor plasma.

29. The system of claim 27 wherein the optical detector comprises means for focusing at least the optical component of the resultant radiation, the means for focusing at least the optical component being located a distance from the sensor plasma.

30. The system of claim 27 wherein the optical component of the resultant radiation comprises a harmonic of a fundamental frequency of the optical probe beam, and the optical detector further comprises an optical filter for attenuating a component of the resultant radiation comprising the fundamental frequency of the optical probe beam.

31. The system of claim 27 wherein the optical probe beam comprises at least one pulse of optical radiation.

32. The system of claim 27 wherein the optical probe beam comprises an optical radiation component having a fundamental frequency and a harmonic optical radiation component having a frequency that is harmonically related to the fundamental frequency.

33. The system of claim 27 wherein the optical detector comprises a photomultiplier tube or a photodiode.

34. The system of claim 27 wherein the emitter plasma is located more than thirty meters away from the source of the optical pump beam.

35. The system of claim 27 wherein the sensor plasma is located more than thirty meters away from the optical detector.

36. The system of claim 27 wherein the optical detector is located more than thirty meters from the targeted object.

37. The system of claim 27 wherein the targeted object comprises an explosive material or a biological agent or a chemical agent that is harmful to humans.

38. The system of claim 27 wherein the volume and the another volume overlap.

39. The system of claim 27 further comprising a spectroscopy signal processing unit for analyzing the optical component of resultant radiation detected by the optical detector.

40. The system of claim 39 further comprising an imaging signal processing unit for producing a spectroscopy image from spectroscopy analysis information provided by the spectroscopy signal processing unit.

41. A method of analyzing a remotely-located object comprising:
 inducing a volume of an ionized ambient gas to emit pulsed terahertz radiation directed toward a targeted object by focusing an optical pump beam in the volume;
 focusing an optical probe beam in the volume of the ionized ambient gas; and
 detecting an optical component of resultant radiation produced from an interaction of the focused optical probe beam and an incident terahertz wave in the volume of the ionized ambient gas, the incident terahertz wave being produced by an interaction of the pulsed terahertz radiation with the targeted object.

* * * * *